(12) United States Patent
Jeon et al.

(10) Patent No.: US 6,883,559 B2
(45) Date of Patent: Apr. 26, 2005

(54) METHOD AND APPARATUS FOR GRADIENT GENERATION

(75) Inventors: Noo Li Jeon, Irvine, CA (US); Stephan K. W. Dertinger, Munich (DE); Daniel T. Chiu, Seattle, WA (US); Insung S. Choi, Daejeon (KR); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/690,475

(22) Filed: Oct. 21, 2003

(65) Prior Publication Data

US 2004/0129336 A1 Jul. 8, 2004

Related U.S. Application Data

(62) Division of application No. 09/954,710, filed on Sep. 18, 2001, now Pat. No. 6,705,357.
(60) Provisional application No. 60/233,142, filed on Sep. 18, 2000.

(51) Int. Cl.$^7$ ................................................ B65B 3/00
(52) U.S. Cl. ......................... 141/9; 141/100; 141/236; 141/240; 141/286; 222/132
(58) Field of Search ..................... 141/9, 100, 105–107, 141/236, 237, 240, 285, 286; 222/132, 145.1, 145.5; 137/266, 806, 814, 822

(56) References Cited

U.S. PATENT DOCUMENTS

| | | | |
|---|---|---|---|
| 3,417,770 A | * | 12/1968 | Denison ..................... 137/806 |
| 4,074,687 A | | 2/1978 | Joyce |
| 4,465,583 A | | 8/1984 | Lovegrove |
| 4,966,792 A | | 10/1990 | Terai et al. |
| 5,597,480 A | | 1/1997 | Zhou |
| 5,728,457 A | * | 3/1998 | Frechet et al. ........... 428/310.5 |
| 6,296,020 B1 | | 10/2001 | McNeely et al. |
| 6,645,432 B1 | | 11/2003 | Anderson et al. |
| 6,653,089 B1 | | 11/2003 | Takayama et al. |
| 6,686,184 B1 | | 2/2004 | Anderson et al. |
| 6,705,357 B1 | | 3/2004 | Jeon et al. |

FOREIGN PATENT DOCUMENTS

WO    WO 03/015890 A1    2/2003

OTHER PUBLICATIONS

Dertinger, Stephan K.W. et al., "Generation Of Gradients Having Complex Shapes Using Microfluidic Networks," Anal. Chem., 2001, 73(6), 1240–1246.
Jeon, Noo Li et al., "Neutrophil Chemotaxis In Linear And Complex Gradients Of Interleukin–8 Formed In A Microfabricated Device," Research Article, © 2002 Nature Publishing Group http://biotech.nature.com, published online Jul. 1, 2002, nature biotechnology, vol. 20, Jul. 2002, 826–830.
Jeon, Noo Li et al., "Generation Of Solution And Surface Gradients Using Microfluidic Systems," Langmuir 2000, vol. 16, No. 22, pp. 8311–8316.
Yang, Mengsu et al., "Generation Of Concentration Gradient By Controlled Flow Distribution And Diffusive Mixing In A Microfluidic Chip," Lab Chip, 2002, 2, 158–163.
International Search Report from International Application No. PCT/US01/42195, mailed Apr. 17, 2002.
Written Opinion from International Application No. PCT/US01/42195, mailed Oct. 29, 2002.

* cited by examiner

Primary Examiner—Gregory L. Huson
(74) Attorney, Agent, or Firm—Wolf, Greenfield & Sacks, P.C.

(57) ABSTRACT

A method and apparatus for treating a fluid. A method for treating a fluid may include combining two or more separate streams into a common stream and then splitting the common stream into a new set of separate streams wherein the separate streams may possess different properties. The separate streams may be combined to produce a gradient, such as a concentration gradient or shear gradient. The apparatus of the invention may provide a network of fluidic channels that may be used to manipulate a fluid to produce, for example, a gradient or a series of solutions containing a substance at varying concentrations.

15 Claims, 15 Drawing Sheets

METHOD AND APPARATUS FOR GRADIENT GENERATION

RELATED APPLICATIONS

This application is a divisional of U.S. Pat. No. 6,705,357, issued Mar. 16, 2004, which claims the benefit under Title 35 U.S.C. §119(e) of U.S. provisional application Ser. No. 60/233,142, filed Sep. 18, 2000, both of which are incorporated herein by reference.

FEDERALLY SPONSORED RESEARCH

This invention was sponsored by the National Science Foundation Grant No. ECS9729405. The government has certain rights in the invention.

FIELD OF THE INVENTION

The present invention relates to a method and apparatus for manipulating the composition of a fluid or fluids, and more particularly, to a method and apparatus for producing fluid gradients.

BACKGROUND OF THE INVENTION

Delivery of fluids for industrial, chemical and biological applications has evolved to a point where extremely small, or very large, quantities of fluid can be accurately delivered using a variety of pumping and pipetting techniques. In addition, techniques have been developed for eroding surfaces and for applying chemicals to surfaces in very precise quantities and at specific locations. These techniques may be used to apply solutions and suspensions accurately and evenly over a surface to provide consistent surface chemical densities. However, applications may exist where it is not desirable to introduce or deposit solutions or chemicals evenly, but rather as a gradient where the density of an applied material is greater at one part of a surface than it is at another part of the surface.

Traditionally, linear concentration gradients exhibiting a variation in concentration in relation to distance may be formed by allowing solutes to diffuse from a point of high concentration into a material containing the substance at low concentration. After the substance has been allowed to diffuse for a period of time, a concentration gradient may develop extending away from the point source. The fluid may be sampled at various distances from the point source and progressively lower concentrations will generally be detected as the distance from the point source increases. Unfortunately, because materials in solution continue to diffuse to areas of lesser concentration, the concentration of the substance at any one point changes with time, as does the gradient between any two points. It is therefore difficult to proceed with experiments or processes that require a stable gradient. This problem is compounded when steep gradients are required, as steep gradients generally may decay faster than those that are less sloped.

Gradients on surfaces have been produced by methods using self-assembled monolayers (SAMs) including cross-diffusion, photo-immobilization and electrochemical desorption. However, the types of gradients profiles on surfaces that can be produced, the substances that can be used, and the size of the gradients are all limited.

In addition, known fluid gradients may be limited to linear gradients in which concentration decreases or increases by a constant amount over distance. At times, it may be useful to employ gradient that do not increase or decrease linearly, but rather increase, for example, as a squared, cubed or logarithmic function. However, known point source and linear source diffusion techniques are not known to be capable of producing gradients that exhibit these profiles.

SUMMARY OF THE INVENTION

In one aspect, the invention provides an apparatus comprising a first generation having at least two first generation channels, a common channel providing communication between each of at least two of the first generation channels, and a second generation comprising at least three second generation channels, each of the second generation channels having a first end and a second end with the first end of each being in communication with the common channel.

In another aspect, the invention provides for a method of forming a gradient comprising passing a fluid through a first channel, passing a second fluid through a second channel, joining the first fluid and the second fluid in a common channel, passing fluid from the common channel into at least three additional channels and recombining the fluid from the three additional channels into a single channel under conditions of substantially laminar flow.

In another aspect, the invention provides for a fluid stream comprising a first substance that varies in concentration in a direction that is substantially perpendicular to the direction of the flow of the fluid, and includes a second substance that varies in concentration in a direction substantially perpendicular to the direction of the flow of the fluid, and has a concentration gradient of the first substance that is of a different profile than a concentration gradient of the second substance.

In another aspect, the invention provides for an $n^{th}$ order polynomial concentration gradient where n is greater than or equal to 2.

In another aspect, the invention provides for a surface comprising a first chemical or biochemical gradient disposed on a portion of the surface, a second chemical or biochemical gradient disposed on the portion of the surface and a third chemical or biochemical gradient disposed on a portion of the surface, wherein each of the gradients is different.

In another aspect, the invention provides for a method of treating a surface comprising passing a fluid along a portion of a surface under conditions of substantially laminar flow wherein the fluid comprises a concentration gradient of at least one substance, the concentration gradient being substantially perpendicular to the direction of flow and substantially continuous across a fluid, and treating differentially a plurality of sections of the portion of the surface exposed to different concentrations of the substance.

In another aspect, the invention provides for a method of diluting a fluid comprising feeding a high concentration fluid to a first inlet, feeding a low concentration fluid to a second inlet, passing the fluid from the first inlet and the fluid from the second inlet into a first generation channel, splitting the fluid in the common channel into at least three second generation channels, recombining the fluids from the at least three second generation channels into a second generation common channel, splitting the fluid in the second generation common channel into a plurality of third generation channels, and collecting fluid from at least one of the plurality of third generation channels.

In another aspect, the invention provides for a method of producing a fluid exhibiting two different concentration gradient profiles comprising combining at least a first starting fluid with a second starting fluid to form a combined stream, the first starting fluid comprising a first substance that is substantially absent from the second fluid, dividing the combined stream into a series of second stage streams, and joining at least two of the second stage streams to form a composite stream wherein the composite stream exhibits a different concentration gradient profile for the first substance and a second substance.

In another aspect, the invention provides for a method of producing a series of solutions comprising contacting a concentrated solution of a substance and a less concentrated solution of a substance to form a combined fluid and separating the combined fluid, without using a membrane, into a plurality of separate streams wherein at least one of the separate streams comprises a substance at a concentration that is substantially different than the concentration of the substance in another of the separate streams.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION

Figure 1:
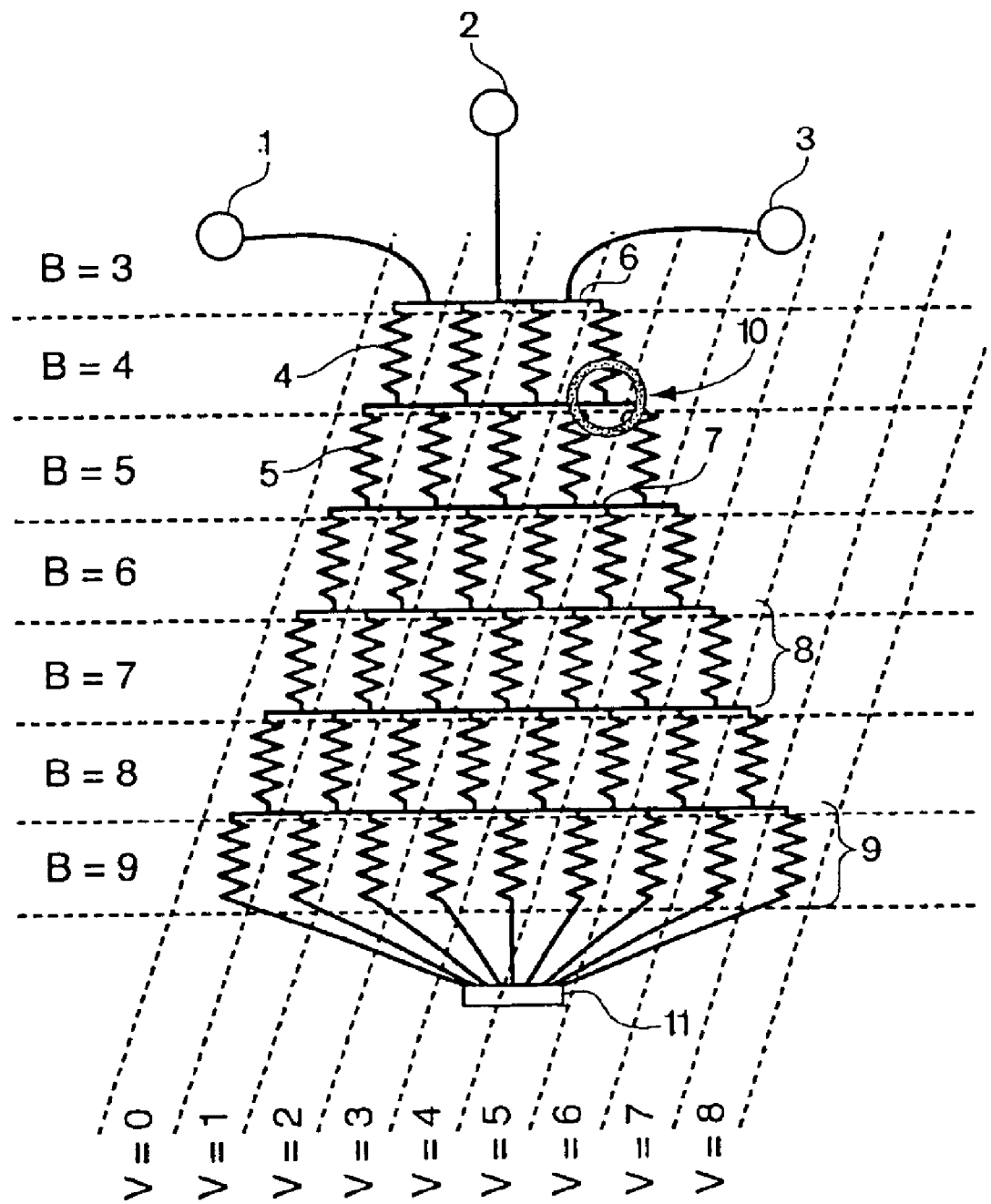
FIG. 1 illustrates schematically a fluidic network including three inlets, nine outlets and a series of serpentine channels.

The present invention provides an apparatus and method for combining and distributing fluids. It may be useful for producing a gradient, particularly in a fluid or on a surface. The method of the invention provides for producing gradients of many types, including concentration gradients, topological gradients and shear gradients. The invention may be particularly useful for producing gradients on a small scale, e.g., gradients covering a span of less than about 10 cm. The method and apparatus provide for linear as well as higher order gradient profiles and these gradients may prove useful in fields such as pharmacology, biology, combinatorial chemistry, proteomics and chip production. The method may be able to provide two or more gradients simultaneously, with each gradient exhibiting the same or a different function. In addition, the invention also provides for the generation of gradients of complex shapes which may be maintained over a period of time.

The present invention provides for gradients exhibiting a variety of profiles, for example, any gradient that may be modeled by a polynomial equation. Traditional point source or line source gradient production techniques may only be capable of providing bell-shaped gradients, and the gradients may decay over a short period of time. By utilizing laminar flow streams and by mixing the contents of the streams through diffusion between the flow streams, the present invention may provide gradients that are more stable.

Laminar flow occurs when two or more streams having a certain characteristic (low Reynolds number) are joined into a single stream, also with low Reynolds number, and are made to flow parallel to each other without turbulent mixing. The flow of liquids in capillaries often is laminar. For a discussion of laminar flow and Reynolds number, see Kovacs, G. T. A., Micromachined Transducers Sourcebook (WCB/McGraw-Hill, Boston, 1998); Brody, J. P., Yager, P., Goldstein, R. E. and Austin, R. H., Biotechnology at Low Reynolds Numbers, *Biophys. J.,* 71, 3430–3441 (1996); Vogel, S., Life in Moving Fluids (Princeton University, Princeton, 1994); and Weigl, B. H. and Yager, P., Microfluidic Diffusion-based Separation and Detection, *Science* 283, 346–347 (1999).

Gradients of the present invention are useful in studying biological phenomena that depend on gradient concentration, such as cell-surface interactions, high-throughput screening using arrays of cells, and in cell-based biosensors. In particular, studies involving chemotaxis, haptotaxis and migration take advantage of the relatively compact and stable gradients achievable by the present invention. As chemotactic cells may be sensitive to concentration differences as small as 2% between the front and back of the cell, gradients with a resolution on the order of a single cell (10–100 $\mu$m, 2–20% per 100 $\mu$m) can be useful. The invention provides the ability to generate gradients of proteins, surface properties, and fluid streams containing growth factors, toxins, enzymes, drugs, and other types of biologically relevant molecules. In addition, gradients of diffusible substances having chemoattractant or chemorepellent properties can play an important role in biological pattern formation, and angiogenesis and axon pathfinding provide examples of processes that can make use of gradients. The invention also provides the superimposition of gradients (similar or dissimilar) of different substances in studying higher organisms. The sawtooth gradients of the present invention can also be used in investigating biological processes.

In one aspect of the invention, two or more fluids, such as gases or liquids, may be joined, mixed and split using a microfluidic network. The microfluidic network may selectively mix and redistribute the fluids to produce a concentration gradient that can be represented by a polynomial equation. The resulting concentration gradient may then be used, for example, to deliver chemicals or biochemicals, treat a surface, or to deposit chemicals or biochemicals on a surface to produce a stationary gradient. It may be preferred that any mixing occur through diffusion rather than through turbulent flow, and the fluidic network may be configured to limit fluid flow to laminar flow at the velocities that are to be applied. By avoiding variations inherent with turbulent mixing, it may be possible to accurately model the mixing that occurs throughout the network and thus possible to predict the profile of the resulting gradient. Furthermore, diffusion of substances between adjacent laminar streams of small size can be accurately predicted, thus providing a technique for designing gradient generators to produce specific spatial gradients. Such predictability may be particularly useful when interfaced with design programs, such as CAD systems, to produce sophisticated gradient generators.

Figure 2A:
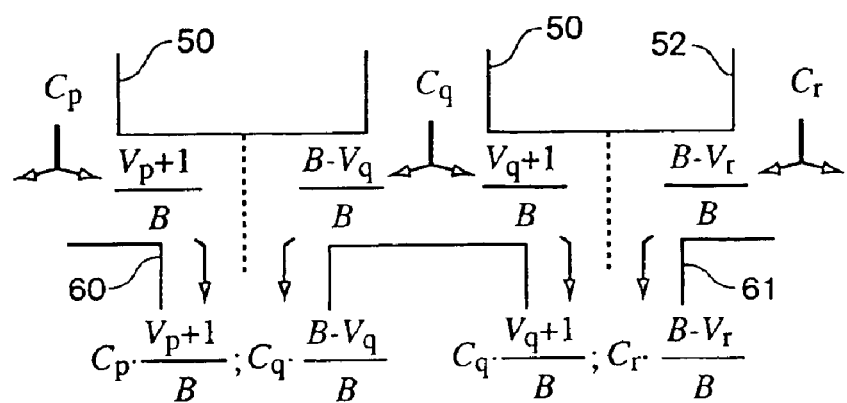
FIG. 2a illustrates schematically how flow is distributed at a branching point of the fluid network of FIG. 1.
Figure 2B:
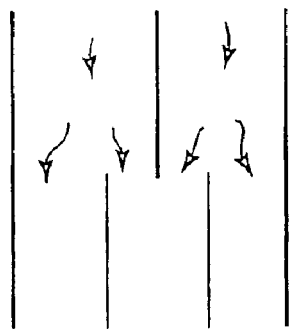
FIG. 2b illustrates schematically how flow is distributed in another embodiment.
Figure 2C:
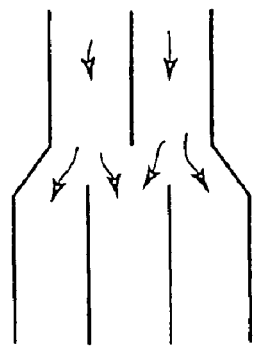
FIG. 2c illustrates schematically how flow is distributed in yet another embodiment.

In one aspect, a microfluidic network having inlets and outlets connected by a series of stages, or generations, may be used. Each generation may include a number of fluidic channels and the fluidic channels in one stage may communicate with the fluidic channels of a subsequent stage by way of a common channel that receives fluid from the channels of one stage and delivers fluid to the channels of a subsequent stage. The common channel may be any area in the network where at least a portion of two distinct fluid streams may come into contact with each other. The common channel may be any size or shape and may be, for example, a distinct channel that is substantially perpendicular to the channels of any adjoining generations, as shown in FIGS. 1 and 2a. In another embodiment, the common channel may simply be an area at the junction of two generations where a portion of one fluid stream may contact a portion of a different fluid stream, as shown in FIGS. 2b and 2c. A design similar to that shown in FIG. 2b may be preferred when the network is to be formed entirely in one large channel, with a series of internal walls separating the various streams.

Subsequent generations may contain a greater number of fluidic channels than previous generations. Such a configuration results in a pyrimidal, or "Christmas tree" design, where fluid flow may start at the top of the pyramid and continue down the pyramid, cascading through a series of generations, each generation including a greater number of fluidic channels than a previous generation.

The individual fluidic channels of a final generation of a network may be joined so that a composite stream is formed with fluid from each individual channel flowing laminarly in the composite stream. The individual streams may be in a plane so that, at most, each stream is in contact with two other streams. Alternatively, the composite stream may also include streams that run above or below other streams in the channel, thus providing a three dimensional configuration wherein a given stream may be in contact with a number of adjacent streams.

In one aspect, the network may be of any design and size that serves to adequately join, split and, in some cases, recombine the split flows into a composite flow. The geometry of the network may be tailored to produce a specific gradient or class of gradients. The network may function by taking two or more fluids, for instance, pure water and a salt solution, and combining the solutions, splitting the solutions and rejoining the solutions to form a composite fluid. When two solutions containing different concentrations of a substance come into contact with each other, the substance will diffuse from the solution of greater concentration into the solution of lesser concentration. For example, salt from a salt solution will be transferred from the salt solution to an adjacent solution containing only water. Thus, two fluid streams in contact with each other may exchange materials back and forth depending on the relative concentrations of the materials in each of the fluid streams. This is clearly a different mixing technique from turbulent mixing where two fluid streams are combined to form a single, homogeneous stream.

By starting with two or more solutions, at least two of which may contain a substance at different concentrations, the network of the present invention may produce a variety of new fluids, each containing the substance at a different concentration. Each concentration may be predictable due to the structure of the network and the conditions under which it is operated. For example, two separate fluids may be injected into a network through two inlets and the two fluids may contact each other in a common channel. If the contact is made under conditions of laminar flow, if there is little or no turbulence, any mixing that occurs between the two may be primarily through diffusion. Thus, if contact time in the common channel is minimized, little or no transfer will occur between the contacting streams and each stream may retain its unique identity and composition.

Furthermore, if fluid from each of the inlets joins a common channel at a "T" intersection, a portion of the solution entering the "T" intersection will pass to the left and a portion of the solution will pass to the right. The component of each of the inlet fluids that passes in each direction at the "T" may be a function of the resistance to flow that the fluid is subjected to in each of the directions passing downstream. Once in the common channel, a portion of the fluid flow originating from one input stream may be contacted with a portion of fluid flow from another input stream resulting in a combined flow of two adjacent laminar streams. If the common channel subsequently leads to another series of new, independent channels, the two starting fluids (the proportion of each depending on the specific location in the common channel) may be fed from the common channel into the new independent channels (at another "T" intersection) according to the relative fluid resistance exhibited by each of the new independent fluid channels. Thus, a network may be arranged so that ⅓ of the fluid flow from a first input passes into a first individual channel and ⅔ of the fluid flow passes to a second individual channel. Fluid passing into the first individual channel may be joined by additional fluid that originated from a different inlet. This may form a combined fluid in the individual channel that is made up of, for example, 50% fluid from the first input stream and 50% fluid from the second input stream. If the combined fluid, consisting of two adjacent streams in laminar flow, is given adequate time to diffusively mix in the independent channel, the exiting fluid may represent a homogeneous solution that contains, for example, substances at a concentration that is an average of the orginal concentration in each of the input streams.

A network may include any number of inlets, a number of connected generations with one or more channels in each generation, and one or more outlets. In general, if a greater number of inlets are employed, a greater complexity of resulting concentrations or concentration gradients may be produced. In one embodiment, it has been empirically determined that the gradient profiles produced may be modeled by a $(n-1)^{th}$ order polynomial where n is the number of inlets feeding the fluid network. For example, if a gradient of the third power is desired, it may be preferable to use a gradient generator that employs four inlets. A linear gradient (which may be considered a first order polynomial), for example, may be achievable with two inlets. As the apparatus of the invention may provide for splitting, combining and recombining fluid streams, a binomial distribution may be obtained, for example, when the splitting ratios at the nodes of the network are 1:1 throughout the network. If splitting ratios are other than 1:1, a polynomial distribution may result. In general, a greater amount of fluid may be channeled to the outer portions of the network when the distance from the splitting nodes to the network's axis of symmetry is greater and when the branched system is of a higher order, containing a greater number of generations.

In one aspect, periodic gradients (gradients exhibiting a repeating profile) may be produced by combining together the output from two or more pyramidal fluidic networks. Each of the networks may share inlets and may operate in parallel, with the output of each network being joined with the output of another network or networks. Alternatively, a periodic gradient may be generated by a single network with a greater number of inlets.

In one aspect of the invention, two or more fluids containing different concentrations of a substance, such as a solute, may be combined, mixed and split to produce a wide variety of gradient types. This may be performed by using an apparatus such as that illustrated in FIG. 1. FIG. 1 provides a schematic representation of a system that includes three inlets, 1, 2, and 3, and a series of serpentine vertical channels, such as 4 and 5. Serpentine channels are channels that take an indirect route, for instance, by making multiple turns back and forth of greater than 90°. Thus, serpentine channels may be useful to fit a relatively long flow path into a small area, such as in a microfluidic network. The serpentine channels may be joined by horizontal common channels such as 6 and 7. A row of serpentine channels may be contained in a set referred to as a generation, for example, 8 or 9. The microfluidic network may include any number of inlets, common channels, vertical channels and generations. A generation may include at least two channels, preferably serpentine, generally operating in parallel. Each generation may be any shape, such as the pyramidal design shown in FIG. 1. The microfluidic network also has a number of branching points, 10, at locations where vertical channels intersect common channels. The network may also include a composite channel, 11, which may be connected to each of the vertical channels contained in the final generation. The channels used in the microfluidic network may be of any size and are preferably less than one millimeter in diameter, and most preferably are less than about 100 microns in diameter and most preferably less than 50 microns in diameter. The height of the channel may be equal or different from the width and is preferably less than about 100 microns high.

In operation, fluids containing substances at different concentrations may be introduced into any number of inlets. A pump, for example, a syringe pump, may be used to provide fluid at an adequate flux, pressure and velocity. The flux at each of the inlets may be varied to produce different types of gradients, and, for simplicity, the use of the network in FIG. 1 will be described using three different fluids being introduced at the same pressure and velocities. Fluid entering through inlets 1, 2 or 3 is distributed in common channel 6 and is fed to the serpentine channels in the first generation, for example serpentine channel 4. The serpentine channels in this embodiment are of approximately the same shape and length and therefore exhibit the same resistance to flow. As equal volumes of fluid are being introduced through each of the three inlets and the total volume of fluid is then distributed through four individual serpentine channels, the flow through each of the serpentine channels will be equivalent to ¾ of the flow that is being received from each of the inlets. Likewise, as the fluid advances to the next generation and passes into a set of five serpentine channels in stage 2, the flow in each of the serpentine channels in stage 2 will be ⅘ of the flow through each of the serpentine channels in stage 1, assuming that each of the serpentine channels in stage 2 is of equivalent resistance to flow.

It may be advantageous to predict the output of a microfluidic network so that a network may be fabricated in order to form a specific gradient or gradients. The output of any network can be more easily predicted if the splitting ratio at each branching point within the network can be accurately modeled. If a pyramidal microfluidic network is used, one way of predicting the output of the network is by using the procedure below.

Referring to FIG. 1, a generation, for example 8 or 9, may contain "n" vertical channels and may thus be referred to as an $n^{th}$ ordered branched system (B=n). Each vertical channel within a generation or branch system may be designated as V=0, V=1, V=2 . . . V=B−1. The various flow paths that fluids within the system may take may be dependant, in part, on the resistance of the various channels throughout the system.

If the microfluidic network is produced as illustrated in FIG. 1, vertical channels such as 4 and 5 may provide significantly greater resistance to flow than do horizontal flow channels such as 6 and 7. Accurate flow predictions for such a network may be made by assuming that the resistance in the horizontal channels is negligible when compared to the resistance in the vertical channels. Resistance within a channel may be controlled by a variety of factors, for example, the geometry of the channel including length, width and shape, the structure of the walls of the channel, and the possible inclusion of valves or other constrictions within one or more channels. For equally dimensioned channels, resistance to flow scales linearly with the length of the channel, in Poiseuille flow, and thus if the horizontal channels are much shorter than the vertical channels, for example, ½0th of the length, the resistance to flow in the horizontal channels will be approximately ½0th of that of the vertical channels. In a simple case, illustrated in FIG. 1, the resistance in each vertical channel is approximately the same, thus simplifying the calculations required to determine the flow. The total volume passing through each vertical channel within a generation is equal and to further simplify the analysis, the entire flow from each preceding generation passes into the subsequent generation without further addition or subtraction of flow volume. In a network that is symmetrical left to right as is the network illustrated in FIG. 1, the splitting ratio at each branching point may be approximated by the following ratios. At a branch point where the flow from a vertical channel enters a horizontal channel, the flow to the left may be approximated as [B−V]/[B+1] and the flow to the right of the branch point may be defined as [V+1]/[B+1]. The splitting ratios are illustrated in FIG. 2a which shows the contribution to two of several vertical channels in a subsequent generation that are made by three vertical channels in a preceding generation. In FIG. 2a, $C_p$, $C_q$ and $C_r$ each represent the flow passing through three adjacent vertical channels 50, 51 and 52 in a generation. Thus the flow component passing to the right from $C_p$ is defined as $$\frac{V_p + 1}{B}.$$

Likewise the flow component of $C_q$ that passes to the right at the central branching point is defined as $$\frac{V_q + 1}{B}.$$

The flow component passing to the left from the flow represented by $C_q$ is equal to $$\frac{B - V_q}{B}$$

and the flow component passing to the left from flow $C_r$ may be defined as $$\frac{B - V_r}{B}.$$

In this embodiment, the flow entering into vertical channel 60 may be defined as the sum of the flow component of $C_p$ that passes to the right and the flow component of $C_q$ that passes to the left. Likewise, the flow contributed to vertical channel 61 may be defined as the sum of the flow component of $C_q$ that passes to the right and the flow component of $C_r$ that passes to the left.

Figure 3:
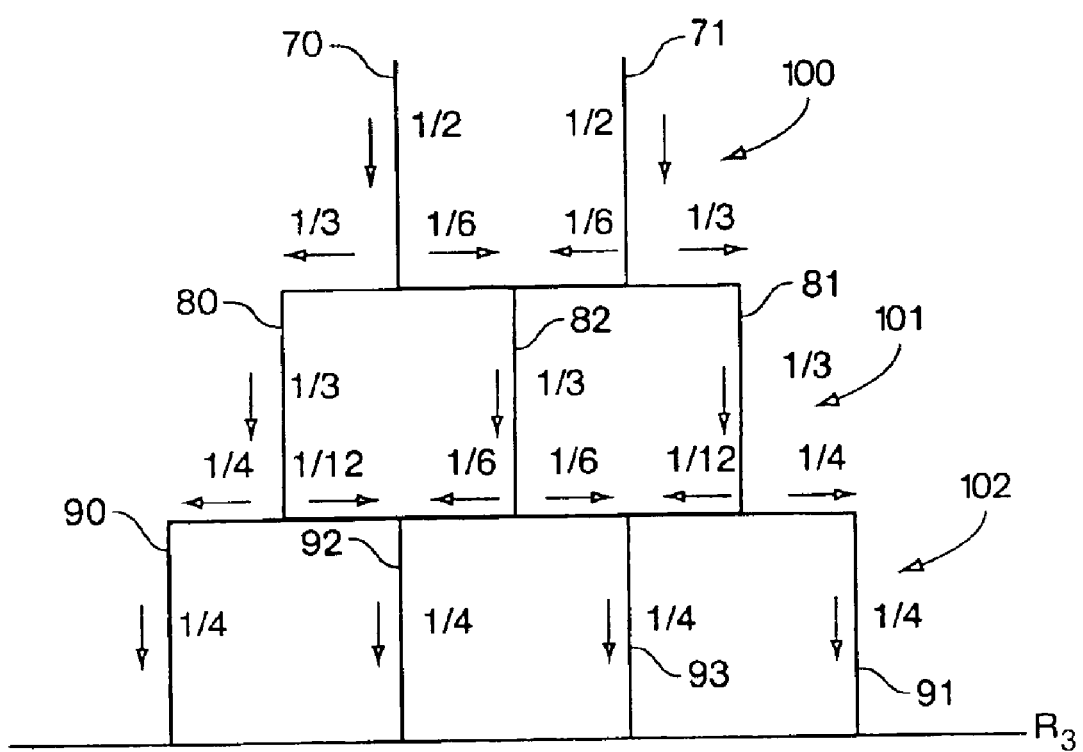
FIG. 3 illustrates schematically how total flow is distributed in a symmetrical fluidic network having two inlets and one additional vertical channel in each successive generation.

FIG. 3 provides a schematic illustration of a two inlet system and provides the actual breakdown of the flow in each of the horizontal and vertical channels in a special case where each of the two inlets provides equal flow to the first stage, each of the vertical channels is of equivalent resistance, and each successive generation includes one more vertical channel than does the preceding generation. The total flow through each stage, or generation, may be represented by the fractions shown in FIG. 3.

As the fluid flow from inlet stage 100 advances to first generation 101, the flow that was originally divided into half in the two inlets is divided into thirds equally (each vertical channel is equally flow resistant) between the three vertical channels at the first generation 101. Thus each vertical channel in the first generation 101 carries ⅓ of the total flow. As each channel in the first generation 101 carries less flow than either of the two inlets at stage 100, the entire flow to exterior channel 80 is supplied by fluid emanating from vertical channel 70 and the entire flow to exterior vertical channel 81 is supplied by vertical channel 71. Therefore, ⅔ of the flow delivered by vertical channel 70 is received exclusively by vertical channel 80 and ⅓ of the flow received from vertical channel 70 (⅙ of the total flow) passes from vertical channel 70 to vertical channel 82. The flow in vertical channel 82 is supplied equally in two parts by the flow from vertical channel 70 and 71 therefore ⅓ of the total flow of vertical channel 71 is received into vertical channel 82. Thus, after complete mixing, vertical channel 82 contains 50% of the fluid passing through vertical channel 70 and 50% of the fluid passing through vertical channel 71. As the entire flow to vertical channel 81 (⅓ of the total flow) is obtained from flow emanating from vertical channel 71, the fluid passing through vertical channel 81 is exclusively that which has passed through vertical channel 71 in the previous stage. Likewise, all of the fluid supplied to vertical channel 80 (⅓ of the total flow) is supplied exclusively from vertical channel 70. Thus, each of the exterior vertical channels 80 and 81 contain fluid of composition equal to that found in vertical channels 70 and 71, respectively, and central vertical channel 82 contains a 50/50 mixture (v/v) of the two fluids supplied by vertical channel 70 and 71. As fluid passes into the succeeding generation, flowing from generation 101 to 102, additional splitting occurs in the centrally located vertical channels of generation 102 but the exterior channels 90 and 91 again contain fluid that has been exclusively supplied by either channel 70 or 71. In this manner, multiple stages may be added to the microfluidic network, and if the number of vertical channels in each successive stage increases by one or more, the outer channels may each contain fluid that has been exclusively derived from one of the first two inlets. In this manner, an entire spectrum of concentrations may be developed including endpoints that are equivalent in composition to the two starting fluids.

Figure 4:
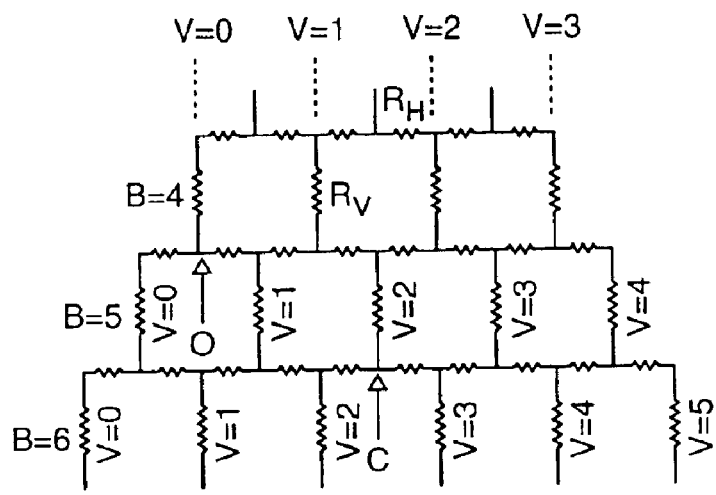
FIG. 4 provides a representational view of a fluidic network illustrating that the network may be modeled by using electrical resistance to represent resistance to fluid flow.

The flow to any microfluidic network such as that shown in FIG. 1 may be accurately modeled by analogizing the flow of liquid through the network with the flow of electricity through an electronic circuit. FIG. 4 illustrates how each vertical and horizontal channel may be represented by an appropriate resistor that reflects the relative resistance to flow through each of the channels. As a result, techniques used to design electrical circuits may also be helpful in designing fluid networks of the present invention. For example, software applicable to the design of electrical circuits may be used to design fluid networks of the present invention.

The geometry of the various components of a fluid network may vary greatly depending upon, among other things, the anticipated capacity of the fluidic network. Preferably, channels within a stage are of a length adequate to provide greater than 90% mixing of two or more fluids that enter the channel and most preferably are capable of providing greater than 99% mixing of fluids prior to the fluids leaving a given channel. As diffusive mixing is a function of time, the residence time of adjacent fluid streams may be important in sizing the components of a network. Residence time within a given channel is a function of, among other variables, fluid velocity, and channel dimensions may be preferably determined after the flow rates anticipated for a particular application have been determined. Flow rates of from 1 to 100 mm/s have been found to provide good results.

In one embodiment, fluid mixing channels are about a centimeter long and in another embodiment are approximately one millimeter in length. Fluid channels as long as 10 centimeters, or longer, may be applicable for networks utilizing large fluid volumes or, for example, when particularly fast rates of fluid flow are preferred. The diameter of fluid channels may also vary and preferably is less than about 1 millimeter in diameter. Most preferably the fluid channels are about 100 microns in diameter and in another embodiment may be smaller than 50 microns and even as small as 10 microns in diameter. As smaller diameter channels may provide for laminar flow at high flow velocities, much smaller diameter channels may be desired and sizes may be limited only by what production techniques are capable of producing. The geometry of the fluid network may be optimized for specific applications and it may be preferable that vertical channels within the network are serpentine or convoluted so that channels of relatively long length may be contained within a small area. In addition, fluid channels may loop back on themselves at different levels in order to minimize the total area occupied by the fluidic network.

The fluid channels, in cross section, may be of any shape suitable for carrying a fluid. For example, the fluid channels, in cross-section, may be circular, square, oval or rectangular. Channel walls may be coated with, or made of, hydrophilic (for water-based applications) or lipophilic (for water insoluble applications) material to minimize boundary effects.

The number of stages, or generations, within a fluidic network is limited only by the size of the substrate on which the fluidic network is disposed. The greater the number of generations, the more refined may be the resultant gradient profile. Networks including 3, 9, 10, 20 or more than 50 generations may be used to produce progressively finer gradients.

The fluidic networks of the present invention may be made in a number of ways, including molding and machining. In addition, a network may be quickly produced by joining a series of tubes or micro-tubes together to arrive at the desired configuration. In addition, fluidic networks may be produced in a modular fashion, with different pre-made pieces being joined together to build a network.

In one aspect of the invention, a microfluidic network may be fabricated in poly(dimethylsiloxane) (PDMS) using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist (MicroChem), to produce a negative master of the photoresist on a silicon wafer. A positive replica of PDMS may be made by molding the PDMS against the master, a technique known to those skilled in the art. To complete the fluidic network, a flat substrate, for example, a glass slide or silicon wafer, may be placed against the PDMS surface and may be held in place by van der Waals forces, or may be fixed to the PDMS using an adhesive. To allow for the introduction and receiving of fluids to and from the network, holes (for example 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue.

Figure 5:
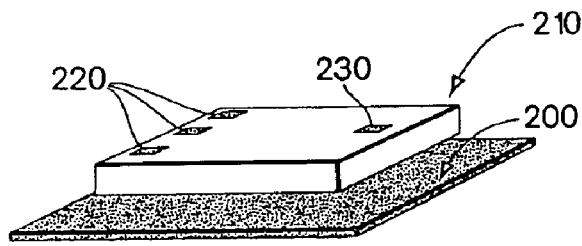
FIG. 5 illustrates a top view of a gradient generator.
Figure 6:
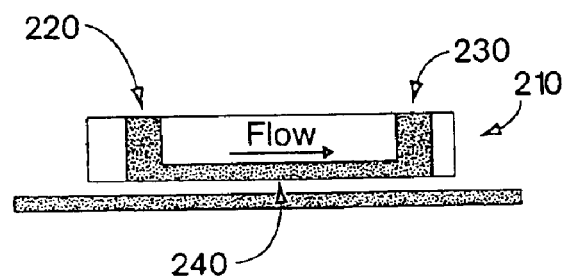
FIG. 6 illustrates a cutaway side view of the gradient generator of FIG. 5.

FIG. 5 illustrates an embodiment of the apparatus of the present invention. A PDMS replica 210 including three inlets 220 and an outlet 230 is contacted with silicon wafer 200 to form a sealed fluidic network. FIG. 6 provides a cut-a-way side view of the embodiment of FIG. 5 showing inlet 220, outlet 230 and fluid network 240 connecting inlet 220 to outlet 230.

Figure 7:
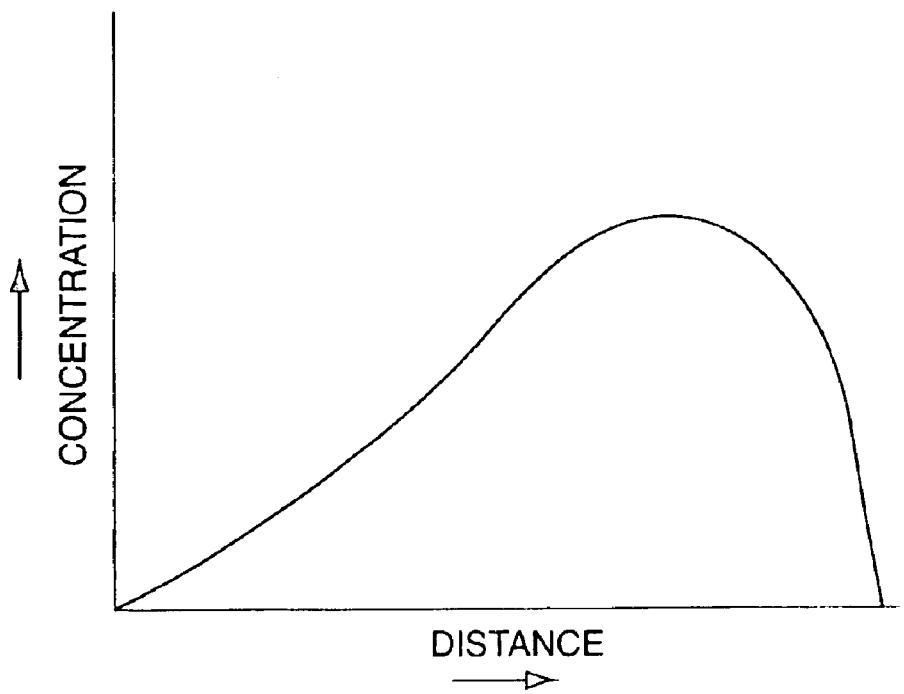
FIG. 7 illustrates graphically a theoretical concentration gradient.

In another aspect, the present invention provides a concentration gradient exhibiting a variation in concentration of a substance in a fluid in relation to distance. The gradients may be formed in any fluid, including gases and liquids, and may represent the concentration of a substance that is, for example, dissolved or suspended in a fluid. A concentration gradient may be represented by a profile that illustrates the concentration of a particular substance or condition at various positions within a fluid or on a surface. FIG. 7 illustrates a concentration gradient profile showing how the concentration of a substance may vary with distance from a given point. In one aspect, a concentration gradient is produced in a direction perpendicular to the flow of a fluid. Such a concentration gradient may be stabilized to provide a constant or relatively constant concentration at any position across a fluid stream, for example, a specific gradient may be maintained in a fluid stream for a second, 10 seconds or a minute, or, alternatively, the concentration gradient may be dynamic so that it changes with time.

In one aspect, a concentration gradient may be formed by joining two or more fluid streams under laminar flow conditions. When two adjoining streams come together under laminar flow conditions, the primary mode of transfer of material between the two streams is through the mechanism of diffusion. Thus, as two streams are joined together, substances in a higher concentration stream will diffuse into the lower concentration stream at a rate that can be accurately predicted. For example, if two laminar flowing streams, one containing a substance at a high concentration and the other containing the same substance at a low concentration, are in fluid contact with each other, eventually the concentration of the substance in both of the adjacent streams will be equalized. However, by controlling parameters such as concentration, fluid velocity, temperature, and fluid stream size, a concentration gradient between the two adjacent streams may be maintained at a constant profile at any chosen point along the path of flow. Thus, a concentration gradient showing a very sharp, two-step profile may be realized immediately after the two fluid streams are in contact, and the concentration gradient profile may be gradually smoothed as the flow of the two adjacent streams progresses until the concentration gradient profile may reach a point where it is flattened and the concentration of the substance in both streams has been equalized. The time required for complete equilibration can be estimated by solving the diffusion equation in one dimension in finite media taking into account the initial distribution for a particular case. An analytical solution for this problem is given by (Eq 1)

$$C(t, x) = \frac{1}{2}C_0 \sum_{n=-\infty}^{\infty} \left\{ \text{erf}\frac{h + 2nl - x}{2\sqrt{Dt}} + \text{erf}\frac{h - 2nl + x}{2\sqrt{Dt}} \right\} \quad (1)$$

where C(t, x) is the concentration at time t and at point x, D is diffusion coefficient in cm$^2$/s, t the time in s, l the width of the channel, h the width of the initial distribution, and $C_n$ the initial concentration in the channel. A numerical evaluation using the first 21 terms in the sum (n=−10 to +10, D=5×10$^{-6}$ cm$^2$/s, width 50 μm, width of initial distribution 25 μm) shows that 97% diffusive mixing is reached after 1 s. We define percent mixing across a channel of width l and at time t as:

$$\% \text{ mixing}(t) = \left(1 - \frac{\int_0^l |C(t) - C(\infty)| dx}{\int_0^l |C(0) - C(\infty)| dx}\right) \times 100\% \quad (2)$$

where C(t), C(∞), and C(0) are the concentration profiles across the width of the channel at times t, t=∞, and t=0, respectively.

A desired profile may be chosen at any point in the spectrum at or between the point where no diffusion has occurred and the point where complete co-mixing has occurred. Moreover, this profile may be accurately and reliably replicated under these same conditions. Any number of fluid streams may be joined together, and when more precise concentration gradients are to be generated, it may be preferred that narrower fluid streams be used. In addition, narrower fluid streams may be less prone to turbulence, and thus the narrower streams may provide for a more stable, repeatable gradient.

Adjacent streams may be joined at a single location or may be staggered to join a composite stream at various points along the flow of the composite stream. In this manner, new substances or higher or lower concentrations of original substances may be introduced to a composite stream after an initial amount of diffusion within the composite stream has already occurred. The adjacent fluid streams need not be equal in size to the other streams that make up the composite stream. Narrower streams are preferred over thicker ones as a smoother gradient will generally be obtained. In addition, a narrower stream may be less turbulent (fluid flow is considered to be turbulent at a Reynolds number of about 2,000 or greater) than is a fluid stream of equal velocity that has a greater cross-sectional area. It is preferred that turbulent mixing be minimized to reduce any variation that may occur in a concentration gradient. Thus, a fluid stream having a width of 100 microns may be preferred over a fluid stream having a width of 1 mm which, in turn, may be preferred over a fluid stream having a width of 1 cm.

By limiting the mixing mechanism to predominantly diffusion, it may be possible (see Equation 2) to maintain a relatively stable concentration gradient in a direction perpendicular to the flow of a composite stream. Thus, although diffusion between adjacent streams may not be stopped, the dynamic flow of adjacent streams may provide for a constant gradient at any specific point along the path of flow. Of course, if desired, the concentration gradient may be altered over time at any specific point by changing any number of parameters, for example, stream concentrations, stream flow rates and the composition of each individual stream.

Figure 8:
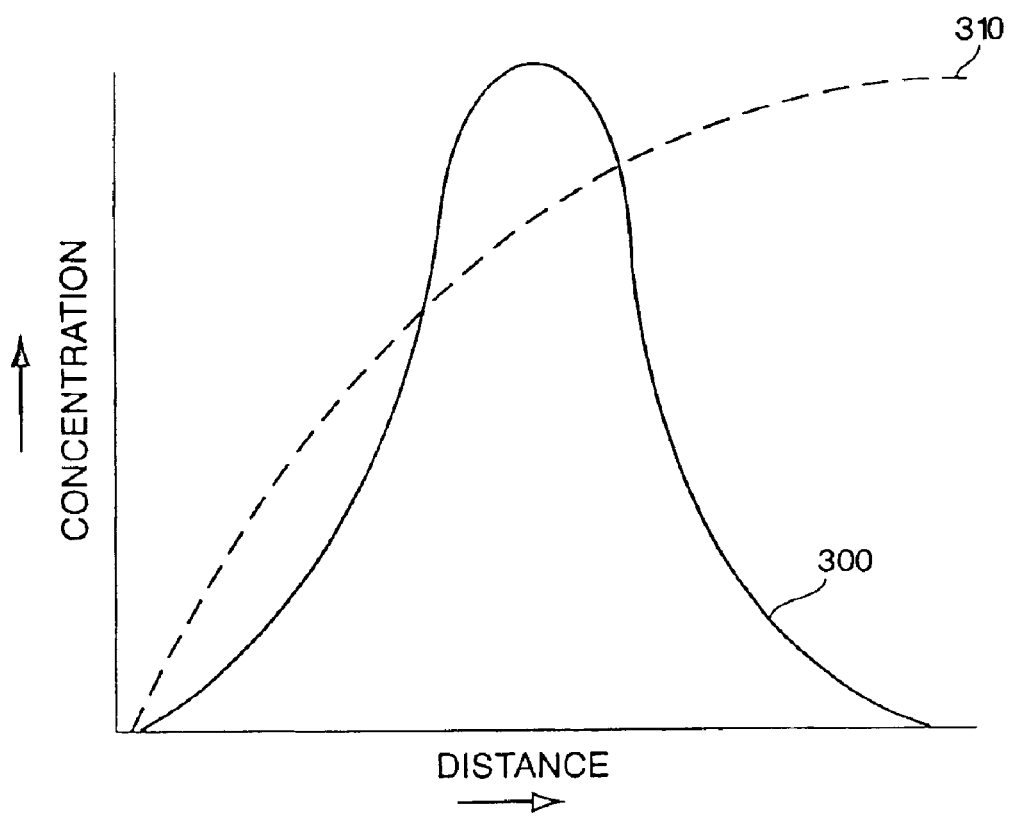
FIG. 8 illustrates graphically two superimposed concentration gradients.

In one aspect, more than one concentration gradient may be formed in a single composite stream. For example, FIG. 8 provides a hypothetical concentration gradient profile for two different substances at the same location along a composite stream. Profiles 300 and 310 represent two different concentration gradients for the two different substances. Profile 300 illustrates a concentration gradient wherein the concentration of the substance is most concentrated near the middle of the stream and decreases towards either edge. Profile 310 illustrates a concentration gradient where the concentration at one edge is zero and increases to a high concentration at the opposite edge with the rate of increase being initially quite high and leveling off as distance from the first edge increases.

In another aspect, concentration gradients in a fluid or on a surface may be varied by adjusting the flow speed of the composite stream. For example, a gradient may be dynamically altered by combining two or more streams in laminar flow, allowing at least some diffusion to occur from one of the individual streams into an adjacent stream, and then adjusting the flow rate of the composite stream to alter the position along the stream where a particular concentration gradient is realized. FIG. 9 provides three different micrographs of an identical fluid stream flowing at three different velocities. The micrographs were taken of a composite stream composed of nine individual streams that were combined into a composite stream. The position where the micrographs were taken is equivalent to position 11 as shown in FIG. 1 of the gradient generator described above. The white dotted lines at the top of each of the three fluorescent micrographs represent the terminus of each of the individual channels, indicating where the nine different individual branches merged to form the composite stream. In the embodiment illustrated in FIG. 9, each of the nine branch channels was approximately 50 microns wide and 100 microns high, and the branches were combined to form a composite stream in a channel that was 900 microns wide and 100 microns high. A solution containing various concentrations of fluorescein isothiocynate (FITC) was passed through each of the nine different channels. Areas of higher concentration appeared as brighter, greener areas in the fluorescent micrographs. The rate of flow in the outlet channel was varied from 0.1 mm/s per second to 1.0 mm/s per second to 10.0 mm/s per second in each of FIGS. 9a, b and c, respectively. The nine individual streams were produced from the gradient generator shown in FIG. 1 by introducing a 5% solution of FITC in water, by weight, into inlet number 2 and introducing pure water into both inlets 1 and 3. The horizontal white dotted line near the bottom of each of the micrographs corresponds to a point that was 500 microns downstream from the junction of the nine independent streams. The fluorescence intensity of the solution was normalized with respect to the starting solution and was expressed in terms of concentration.

The graphs shown below each of the micrographs in FIG. 9 provide the fluorescent intensity across the channel at a point that is 500 microns downstream from the junction point (horizontal white dotted line). The black dots in each of the graphs represent the concentration that was calculated to be in each branch channel if complete mixing in each of the branch channels had occurred. These values were obtained by using the initial concentration of FITC in the flow and using the splitting ratios, obtained as described above.

Figure 9C:
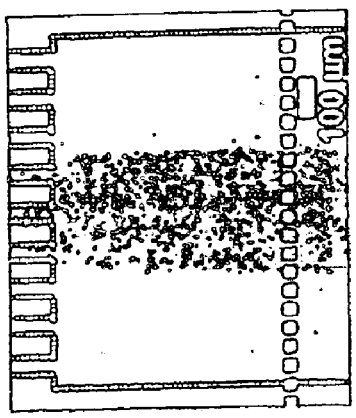
FIGS. 9a, 9a, and 9c illustrate graphically, and with photocopies of fluorescent micrographs, a fluorescent concentration gradient in a composite fluid stream.
Figure 9C:
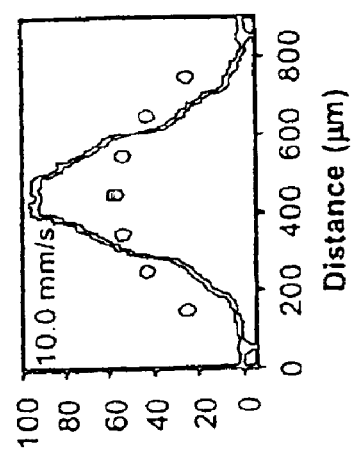
Figure 9B:
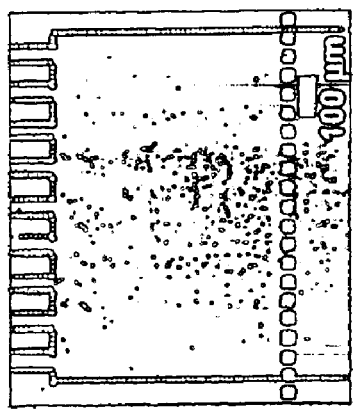
Figure 9B:
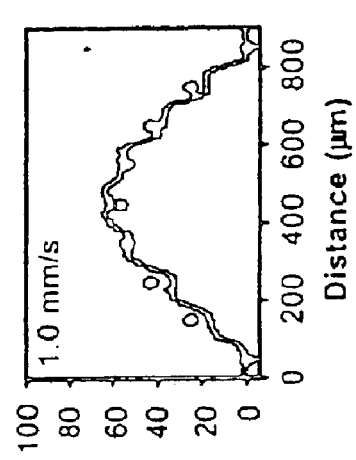
Figure 9A:
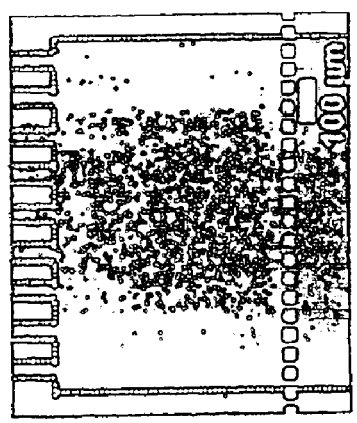
Figure 9A:
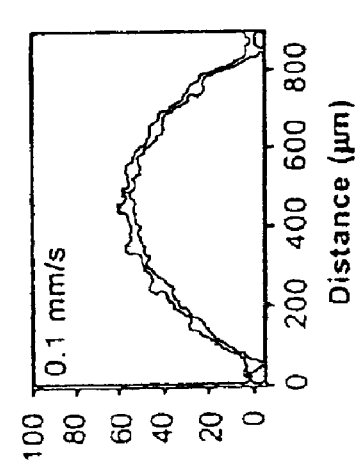

Looking to FIGS. 9a and 9b, the maximum concentration of FITC is found at the center of the composite channel and shows 57% FITC in that region. The outer regions of the same channel indicate 0% FITC or, essentially pure water, as was provided at inlets 1 and 3 (see FIG. 1). As in the other figures provided, both observed fluorescence (green line) and calculated fluorescence (black dots) are illustrated in the graphs. Both FIGS. 9a and 9b exhibit a fluorescence that indicates a concentration that agrees well with the calculated values, and thus indicates that complete mixing of the streams in each of the individual channels has occurred. In FIG. 9a, considerable diffusion has occurred within 500 microns of the point where the nine separate streams were joined. This diffusion is evident in that the borders between each of the nine individual laminar flowing streams have been blurred.

FIG. 9b, however, (a flow rate of 1.0 mm/s per second) shows much less blurring and provides a step-wise gradient as opposed to the smooth gradient of FIG. 9a. Thus, at a flow of 1.0 mm/s per second (FIG. 9a), complete mixing (greater than 99%) has apparently occurred in each individual mixing channel of the gradient generator, however, at this flow rate 500 microns does not provide enough length, or residence time, for enough diffusion to occur to smooth out the stepwise gradient that is seen in the graph of FIG. 9a.

FIG. 9c, however, shows results of the same experiment at a speed of 10.0 mm/s. This micrograph shows that not only has incomplete diffusion occurred in the composite channel, but incomplete diffusion has occurred in at least some of the mixing channels of the gradient generator. Thus, at this relatively faster flow rate, the length of the serpentine channels in the various branches of the gradient generator was not adequate to provide complete mixing of these solutions.

FIG. 10 illustrates an embodiment in which the invention may be used to dynamically vary a gradient. For example, a dynamic gradient may be produced by independently adjusting the flow rate of one or more of the inputs of a fluidic network. If the flow through one of the inputs is either increased or decreased, the change in input flux may dynamically alter the resulting gradient by either increasing or decreasing the effect of the individual input upon the shape of the resulting gradient. As in FIG. 9, the micrographs in FIG. 10 were obtained from a composite stream formed from individual streams of solutions of FITC and water passing through a microfluidic network. As in FIG. 9, three inlets were used, the left inlet carrying pure water, the central inlet carrying a 5% (w/w) FITC solution and the right inlet carrying pure water. The network used to produce the output shown in FIG. 10 had a total of fifteen (15) branch channels rather than the nine (9) branch channels that were used in the device of FIG. 9. Each of the channels was approximately 50 microns wide and 100 microns high.

Figure 10A:
FIGS. 10a, 10b, and 10c illustrate, with photocopies of fluorescent micrographs, 3 different concentration gradients generated under different conditions with the same device.
Figure 10B:
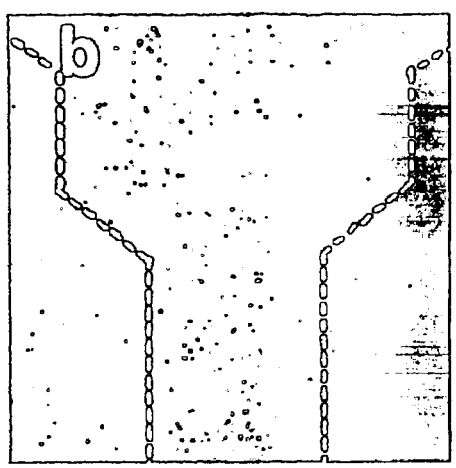

In FIG. 10b, each of the three (3) inlets provided flow to the network at a constant rate of 1 mm/s. A well defined, continuous gradient is evident in FIG. 10b and resembles that shown in FIG. 9a as the area of highest concentration is in the central portion, and areas of lower concentration are evident on either side.

FIG. 10a shows a micrograph taken of a gradient of FITC that is formed when the flow in the left inlet is reduced to 0 and the flow in the middle and right hand inlets are both maintained at 1 millimeter per second. As a result, a shift to the left of the fluorescent FITC solution is clearly evident indicating that the gradient may be altered by adjusting the flow of one of the inlets.

Figure 10C:
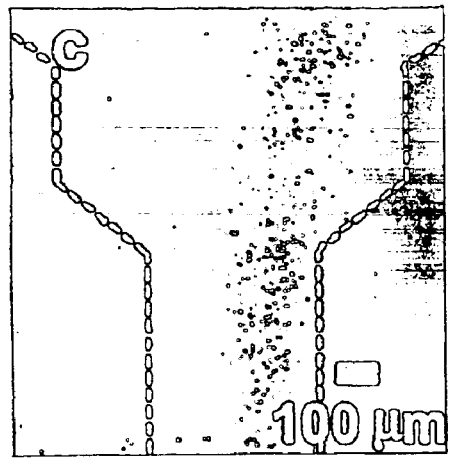

FIG. 10c shows a micrograph illustrating the results when the flow rate in the left inlet has been increased to 3 mm/s while the flow in the middle and right hand inlets were maintained at 1 mm/s. The result in shift in the maximum fluorescence to the right side of the gradient is clearly evident and is likely the result of the increased flow from the left inlet. Thus by altering the flow of just one of the inlets, the gradient may be shifted left or right. By altering the flow of more than one of the inlets, a variety of gradient profiles may be obtained.

FIG. 10 also illustrates how a gradient profile may be compressed or expanded by altering the geometry of the channel through which the gradient flows. In each of FIGS. 10a, b and c (and in the other figures provided) the direction of flow is from the top to the bottom. A cross-sectional dimension of 750 microns was reduced by 50% down to 375 microns by changing the width of the outlet channel. Thus, each individual stream first contributes about 50 microns of width to the gradient and after the constriction to 50% of the original width, each individual stream contributes about 25 microns to the width. Thus, a more compact gradient may be obtained by constricting the flow of the composite stream. As total flux remains constant, the velocity must necessarily increase when the flow is constricted. Likewise, the channel may be expanded to result in a broadening of the gradient and multiple constrictions and expansions may be used in any given channel. In addition, by combining these constriction and expansion options with three dimensional microfluidic networks, an additional level of control is provided to allow the user to create a greater variety of gradients.

Figure 11C:
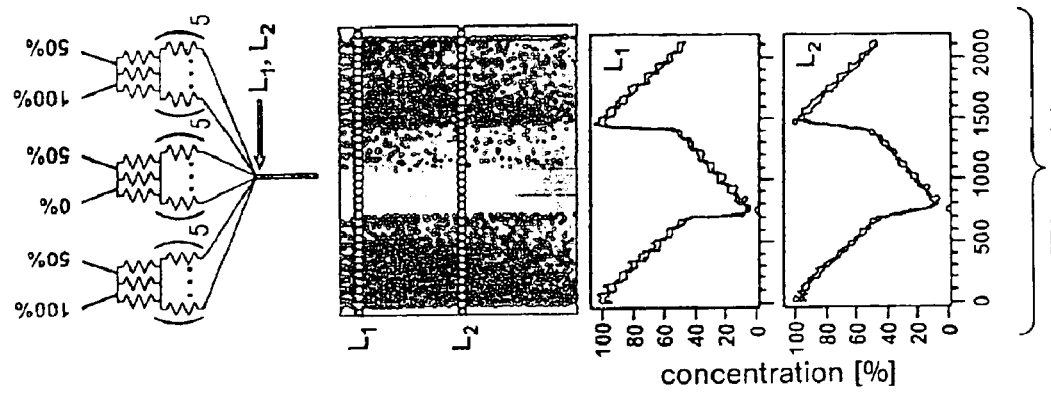
FIGS. 11a, 11b, and 11c illustrate graphically, and with photocopies of fluorescent micrographs, periodic concentration gradients generated by combining the output of three fluid networks, each network having 2 inlets and 8 outlets.
Figure 11B:
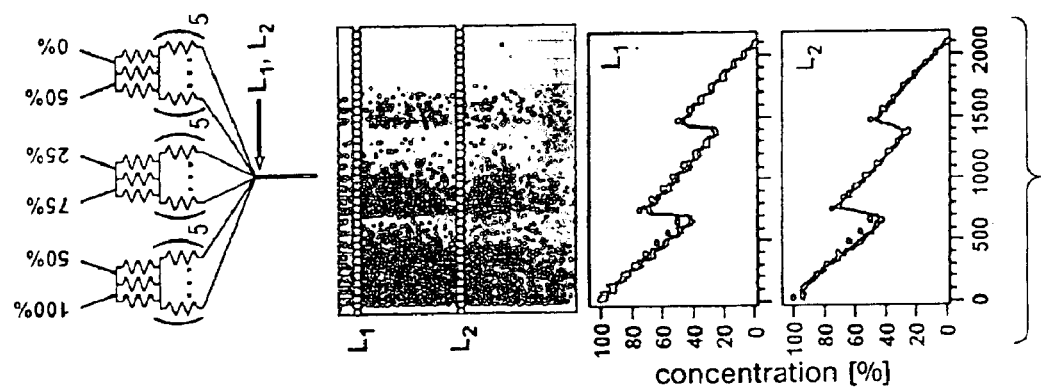
Figure 11A:
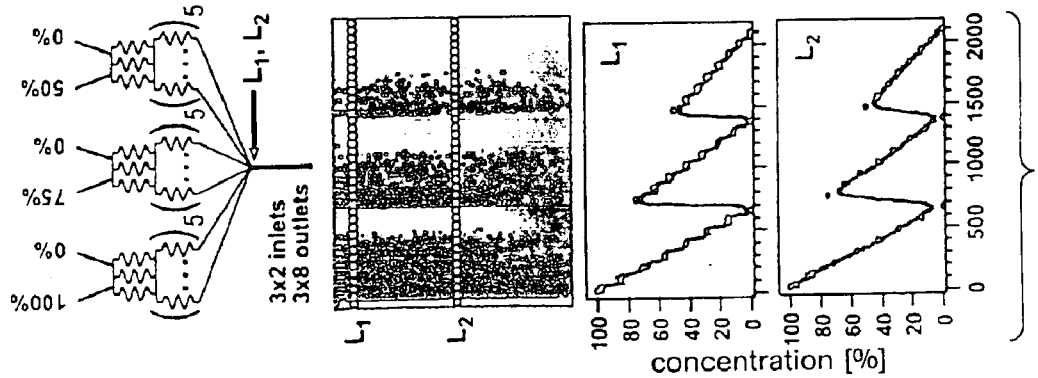

Each of the gradients shown in FIGS. 11a, b and c were obtained by combining the output of three microfluidic networks each of the networks having two inlets and eight outlets. The percentages at the top of each of FIGS. 11a, b and c indicate the concentration of FITC in each solution that is being supplied to each inlet for each individual network. 100% represents a 5% solution of FITC in water. Point $L_1$ in each of FIGS. 11a, b and c is a point in the channel immediately following the point where individual streams are joined to form a composite stream. $L_2$ represents a point 800 microns downstream from $L_1$. In each of the figures, at $L_1$ the individual steps in the concentration profile can be observed directly from the micrograph and are also evident in the graphs at the bottom of each of the figures. This resulting step-wise gradient occurs when little or no diffusive mixing has occurred across the boundaries between adjacent individual streams. In contrast, at $L_2$ (800 microns downstream at a flow rate of 514 microns per second, 1.56 seconds after joining) a significant amount of diffusion has occurred, thus smoothing the gradient profile. The steps are no longer evident either visually from the micrographs or graphically in the graphs shown below each micrograph. Using a value of $D=2.6 \times 10^{-6}$ cm$^2$ as a diffusive coefficient, (the diffusive coefficient of Rhodamin 6G which is structurally similar to FITC and with comparable molecular weight) it is predicted that the profile should have a periodicity of 90 microns and should decay after a time of about 1.5 seconds. This is confirmed empirically in the micrographs. FIG. 11a illustrates a saw tooth gradient where both the amplitude of the peak and the slope of each individual linear gradient decreases from left to right. In FIG. 11a, the periodic gradient was generated by passing pure water through 1 of the inlets in each of three networks and a solution containing 100%, 75% and 50% FITC in water and each of the respective networks passing from left to right. FIG. 11b illustrates a periodic gradient that may be obtained when solutions of 100% and 50%, 75% and 25%, and 50% and 0% are input into each of the three networks respectively. FIG. 11c illustrates a periodic gradient that may be formed using both negatively and positively sloped linear gradients. Such a gradient was obtained by inputting concentrations of 100% and 50%, 0% and 50%, and 100% and 50% in each of three networks, respectively. Each graph shows the concentration percent represented by each individual stream at various points across the channel width. The x axis provides the point from left to right at which each of the readings were taken within the channel. Positions are given in microns from the left side of the composite channel.

Figure 12A:
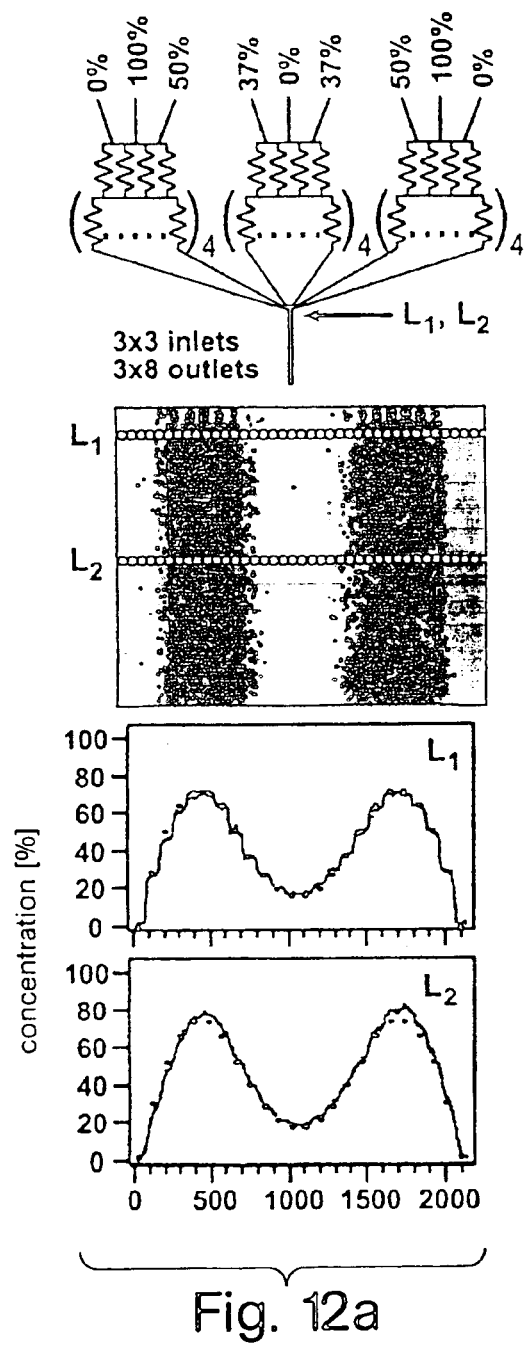
FIGS. 12a and 12b illustrate graphically, and with photocopies of fluorescent micrographs, periodic concentration gradients generated by combining the output of three fluid networks, each network having 3 inlets and 8 outlets.
Figure 12B:
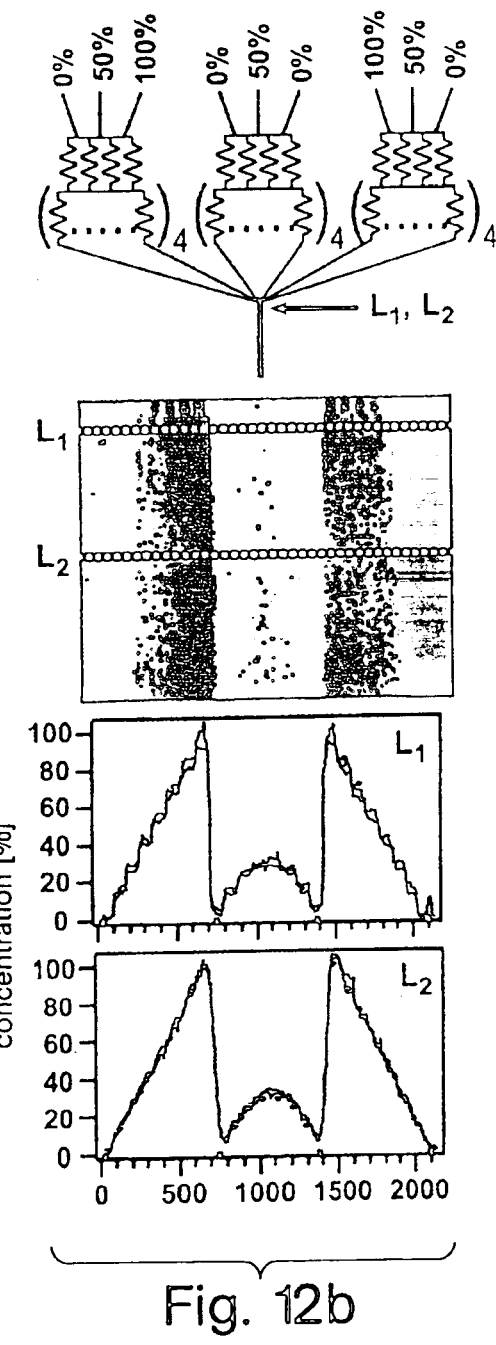

FIG. 12 illustrates experimental results achieved when three networks were combined to produce a gradient, each of the networks having three inlets. Using three inlets, a parabolic gradient profile (second order polynomial) may be constructed, and an example is illustrated in FIG. 12a showing how three (3) parabolic gradients may be joined together to form a unique composite gradient. FIG. 12b illustrates an example where two linear gradients have been combined with a parabolic gradient to generate a composite gradient consisting of both linear and second order profiles. In both FIGS. 12a and 12b fluorescence expected and detected at the point of stream convergence ($L_1$) and at 800 microns downstream from point $L_1$ ($L_2$) is given. As in FIG. 11, a greater amount of diffusion has occurred at point $L_2$, thus smoothing the stepwise gradient into a continuous gradient.

Figure 13C:
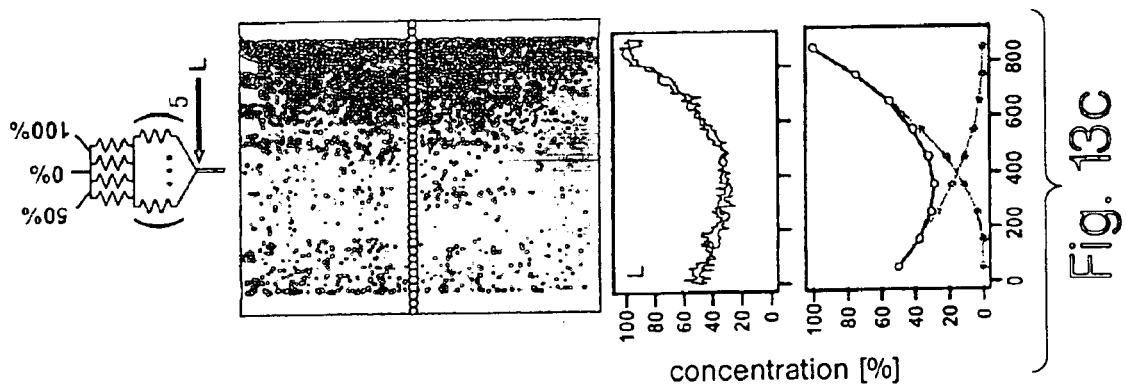
FIGS. 13a, 13b, and 13c illustrate graphically, and with photocopies of fluorescent micrographs, single component concentration gradients generated by individual fluid networks having 3 inlets and 9 outlets.
Figure 13B:
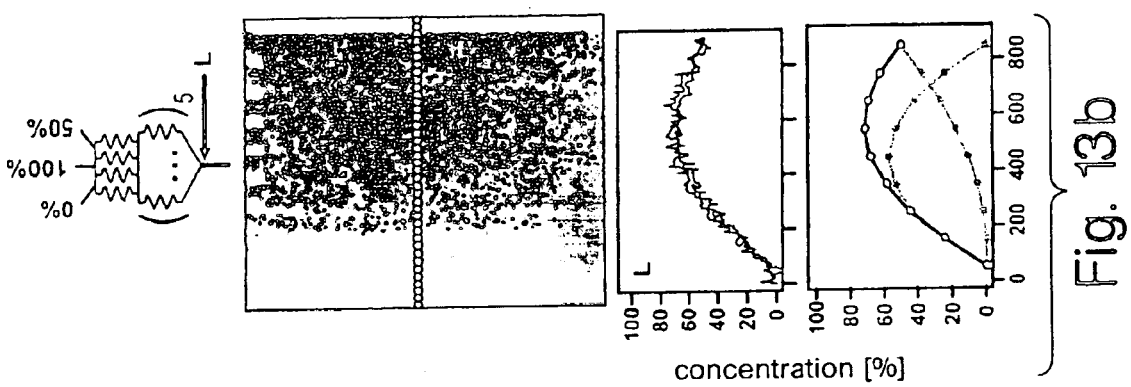
Figure 13A:
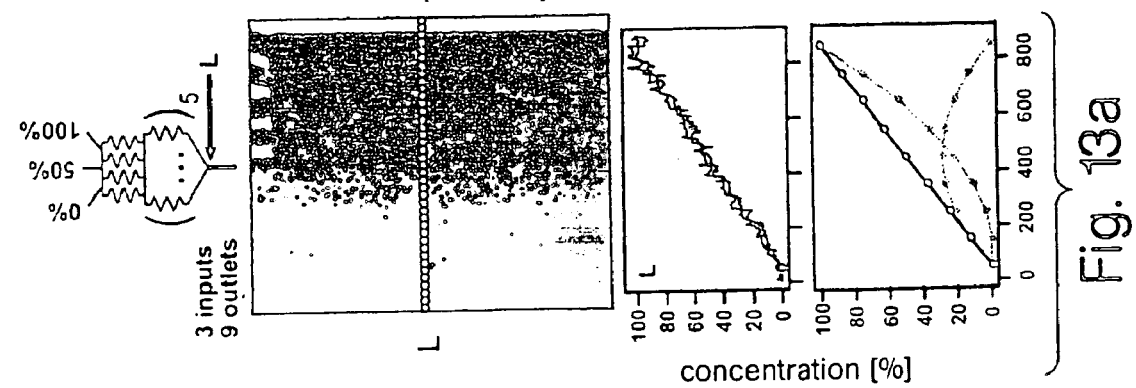

FIG. 13 illustrates some of the profiles that may be obtained from a microfluidic network having three (3) inputs and nine (9) outlets. Each of FIGS. 13a, b and c were obtained by permuting the order at the inlets of three different solutions containing 100%, 50% and 0% fluorescine (normalized) in 100 mM $NaHCO_3$ buffer at pH 8.3. The solution input at each individual inlet is provided at the top of each of FIGS. a, b and c. Each of the profiles generated can be described by a second order polynomial. The dark line in the bottom graph of each of the figures shows the calculated gradient profile. The gray lines and dots in each of the lower graphs illustrate the fluorescine contribution from each of the individual inlets. FIG. 13a illustrates the interesting case where a linear gradient is obtained by superimposing two second order gradients in the same fluid.

In another aspect, the invention may be used to shape the topography of a surface. The gradients provided by the invention may be used to shape a surface by either removing or adding material to the surface. For example, material may be deposited on a surface in proportion to the concentration of the material, or a related material, in a fluid that is passing over the surface. Alternatively, the fluid passing over the surface may contain a substance that removes material from the surface and it may do so in proportion to the concentration of the substance in the fluid. Therefore, if a gradient can be generated in a fluid flowing across a surface, the topography of that surface may be altered in a way that matches, or mirrors, a concentration gradient in the fluid. Materials that may be used to augment a surface include, for example, metals, polymers, salts, ligands and biological materials. Materials that may be used to remove parts of a surface include, for example, acids, bases, etchants and biological materials.

Figure 14:
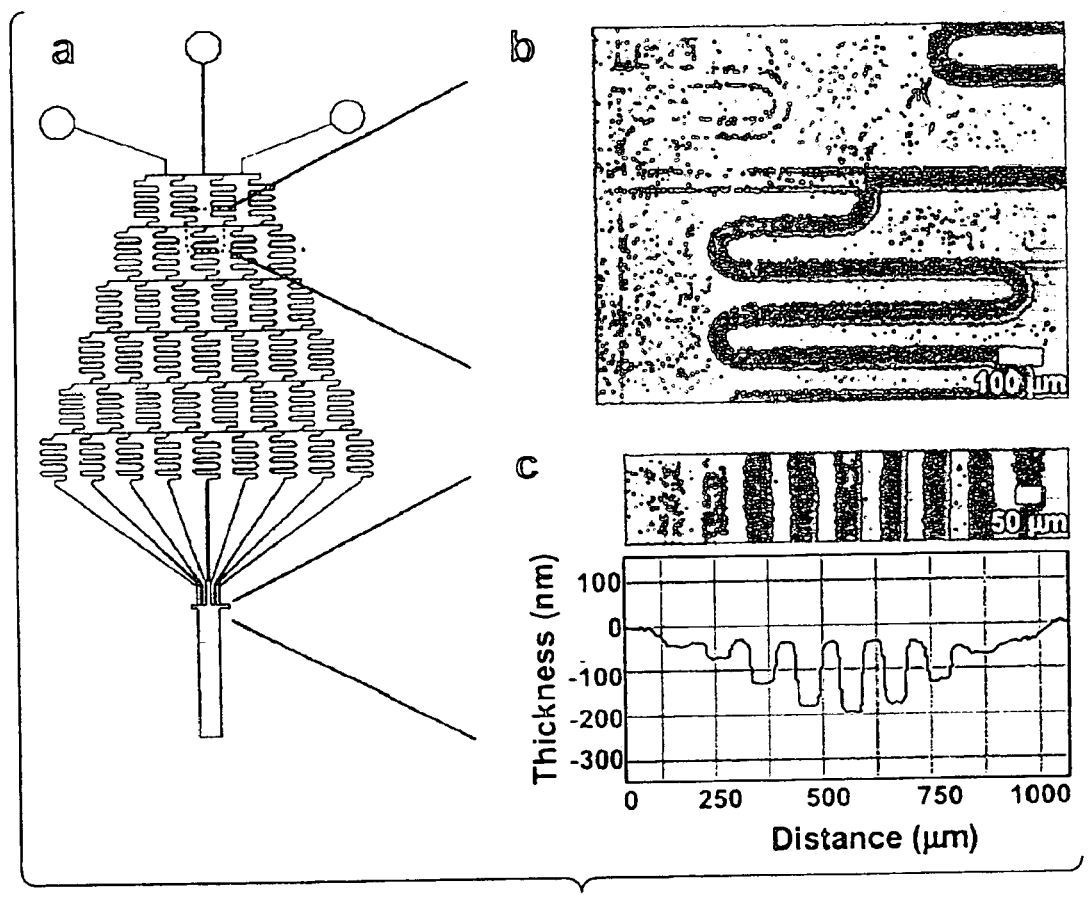
FIGS. 14a, 14b, and 14c illustrate schematically, graphically, and via a photocopy of an optical micrograph, the topological results of distributing an etchant across a network and surface of $SiO_2$.

FIG. 14 illustrates how a topological gradient may be formed by passing a solution of hydrofluoric acid over a silicon dioxide layer disposed on a silicon wafer. FIG. 14a illustrates the microfluidic network that was used to distribute the HF solution. FIG. 14b provides an expanded view of a portion of the network shown in 14a showing a branch point where two separate streams were joined in a common channel and fed to an individual mixing channel in a subsequent generation. Each of the serpentine channels in the network is about 10 millimeters in length, providing an adequate residence time for the fluid in each of these channels to mix exclusively through the mechanism of diffusion. Each of the microfluidic channels in the network is about 50 $\mu$m wide and about 100 $\mu$m high. Proceeding from left to right, a solution containing water was injected into the first inlet, a 5% solution of HF and water was injected into the second inlet, and water was injected into the right inlet. The flow of each inlet stream was kept at 0.1 millimeters per second. HF solutions are known to etch $SiO_2$ and higher concentrations of HF will etch a greater amount of $SiO_2$ and do so more rapidly. The micrograph of FIG. 14b shows with color the different depths that were carved into the microfluidic network. The channel to the upper left in FIG. 14b shows a distinct blue color representing a thickness of about 310 nm of silicon dioxide on the silicon substrate. The upper right channel, in orange, shows a silicon dioxide layer thickness of about 450 nm. When combined in the serpentine channel in the bottom half of FIG. 14b the channel shows a light green color indicating a depth of about 340 nm in the channel containing the combined fluid. Thus, the combination of the stronger and weaker solutions removed material at a rate in between the rate produced individually by the strong and weak solutions. FIG. 14c provides an expanded view illustrating visually the amount of material that was removed from the surface at various locations in contact with nine outlet streams. The depth of each channel indicated in the underlying graph shows the results of a surface profilometer scan that was made across the nine individual channels immediately before the point where they were combined into a single composite channel. Thus, the thickness of the $SiO_2$ layer that can be inferred from the color of the etched channels agrees with the surface profilometer data. These results indicate that a microfluidic network may be predictively designed to produce a chosen topological gradient.

Figure 15:
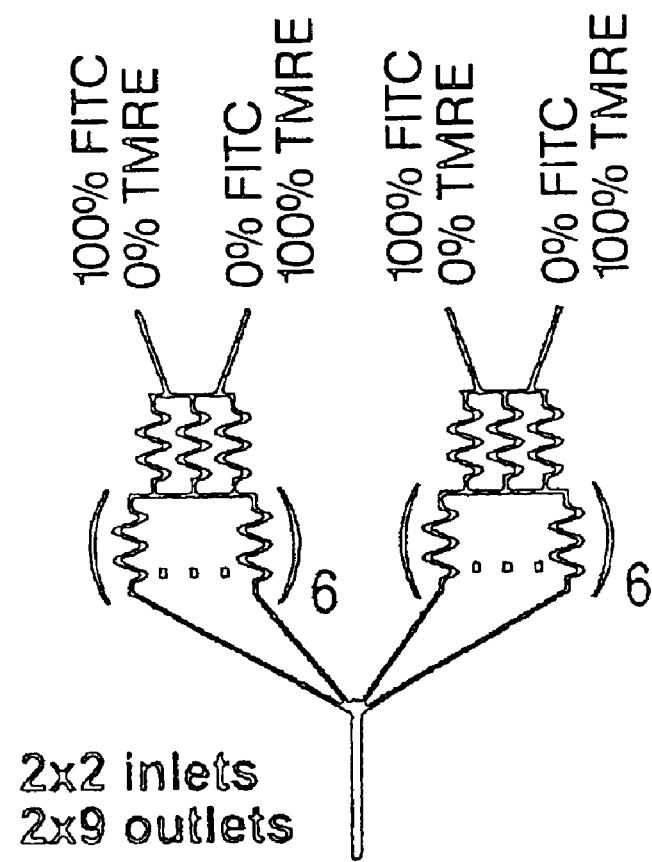
FIG. 15 illustrates via a photocopy of a fluorescent micrograph, a composite gradient formed from combining two chemical gradients, each of the gradients generated by a network having 2 inlets and 9 outlets, and two different fluorescent solutions being supplied to different inlets of each network.
Figure 15:

In another aspect, different shapes may be produced simultaneously to produce several gradients in a single combined stream. FIG. 15 illustrates how the output from two networks, each having two inlets and nine outlets, may be used to combine two saw tooth gradients. Each pair of the inlets for each of the networks was supplied with the same pair of solutions. The inlet on the left was supplied with an ethanol solution of 100% FITC and the inlet on the right was provided with a solution containing 100% tetramethyrhodamine ethylesther, TMRE, in ethanol. Thus, each of the contributing networks provides a linear gradient of each of the fluorescent dyes, the gradient of one dye being the mirror image of the gradient of the other dye. These mirroring linear gradients may then be combined as shown in the FIG. 15 to provide an additional level of complexity to the gradients that may be obtained.

Figure 16:
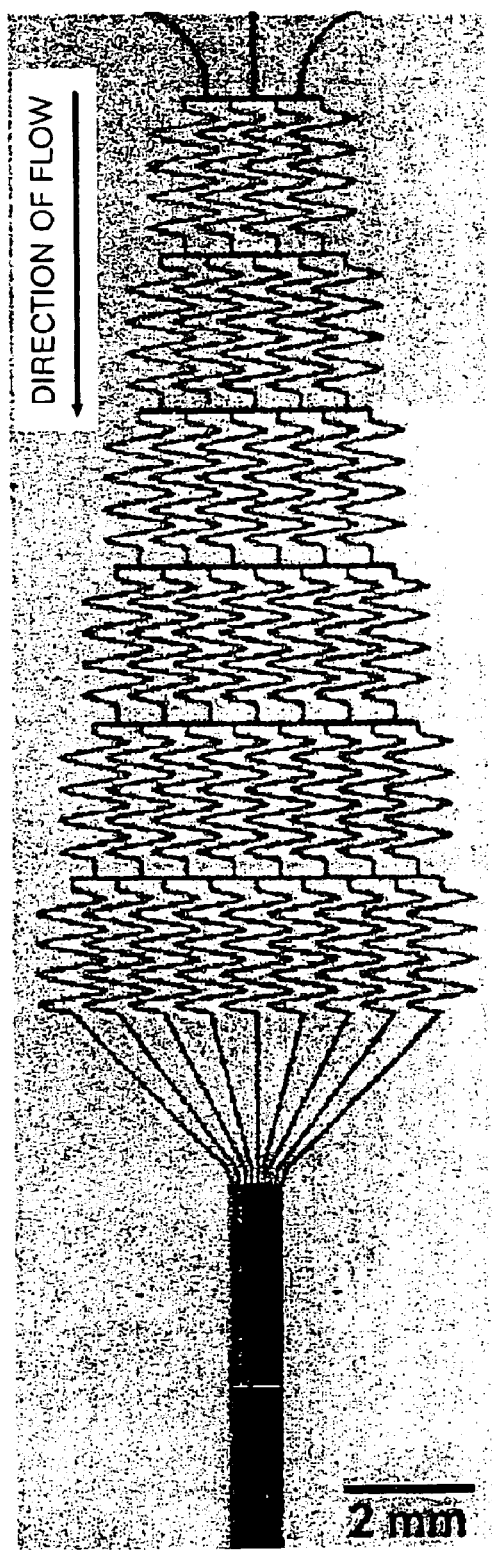
FIG. 16 illustrates via a photocopy of an optical micrograph the diffusional mixing that occurs in a network having 3 inlets, 6 generations and 9 outlets when two different solutions are passed through the left and right inlets and a combined solution is passed through the central inlet.

FIG. 16 provides a micrograph showing an expanded view of a microfluidic network of the present invention having three inlets and nine outlets, the nine outlets being joined to form a composite channel. Using syringe pumps, a green dye (FITC) was injected in the left inlet, a red dye (TMRE) was injected in the right inlet and a 1/1 mixture of both dyes was injected into the central inlet. Each solution was input at the same velocity and flux, representing a flow rate of 1.2 millimeters per second. It is apparent from the micrograph that as the streams of dye traveled down through the network, the streams were split at the nodes, combined with neighboring streams in various ratios and then allowed to mix in the serpentine channels by diffusion. All flow throughout the network was laminar. The outermost channel of each generation retained the vivid color of the fluids input to the left and right input channels and thus the resulting gradient extended from a solution including 100% FITC on the left to 100% TMRE on the right. After the nine individual outlets were joined to form a composite stream, diffusion blurred the stepwise gradient into a more continuous gradient as shown at the bottom of the FIG. 16.

Figure 17A:
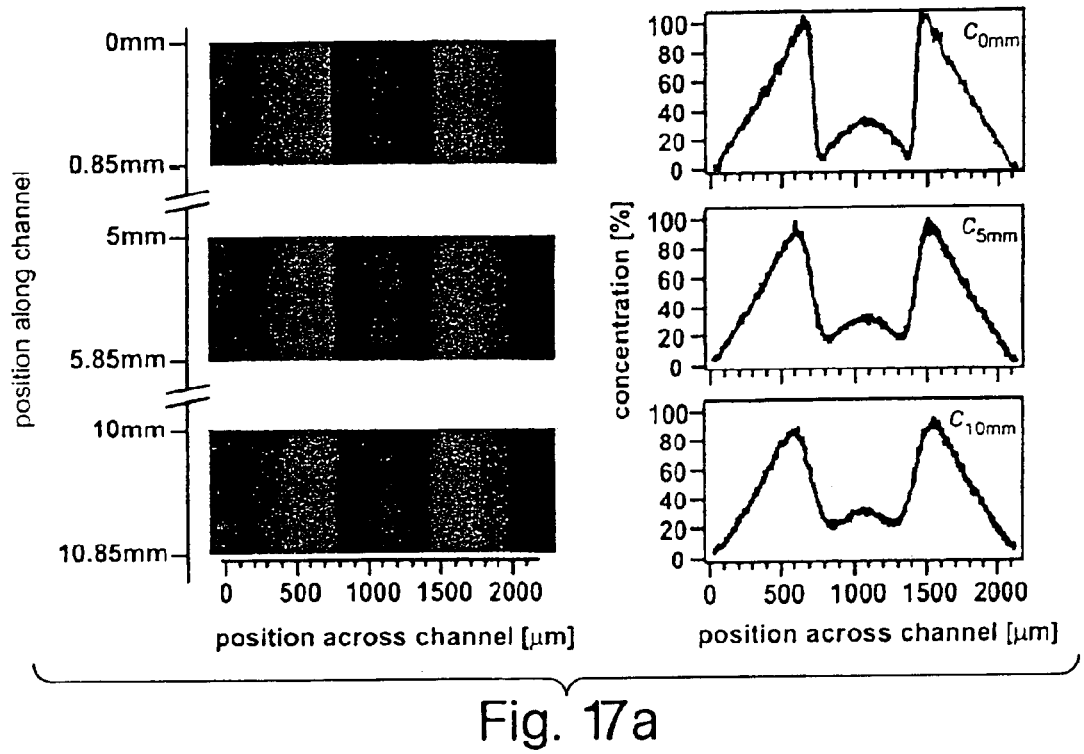
FIG. 17 illustrates graphically and via optical micrographs the blurring that occurs do to diffusional mixing at various points along a flow path of a composite gradient that has been formed from fluids containing FITC.
Figure 17B:
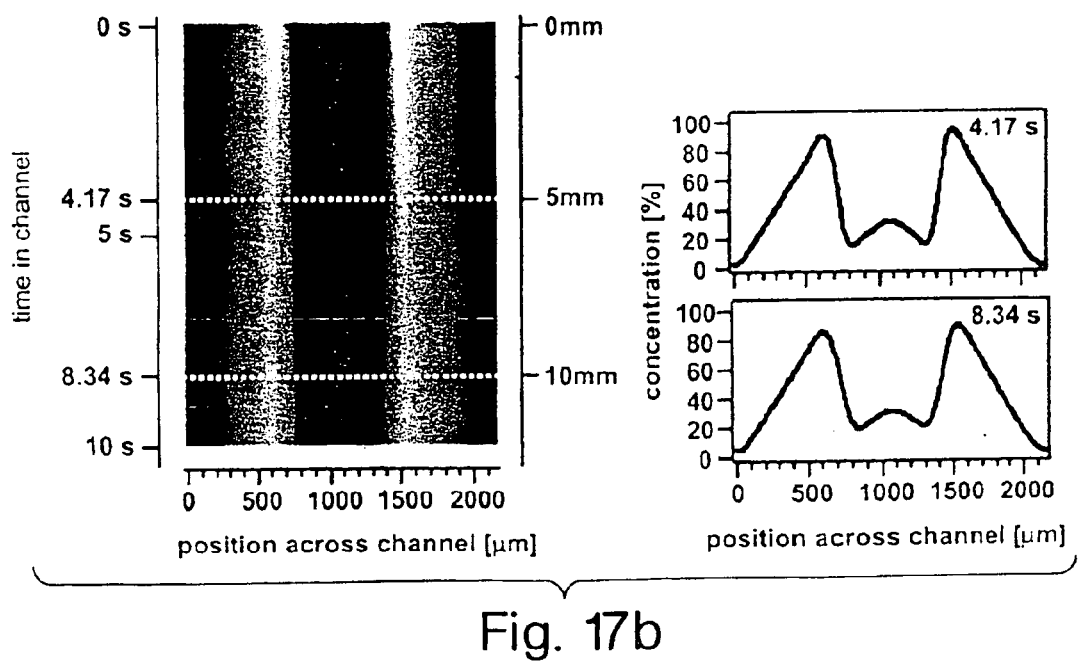

FIG. 17a illustrates the blurring that may occur through the mechanism of diffusion along the concentration profile at three different positions downstream in a channel. Diffusional decay may be described by the diffusion equation in one dimension, $\delta c/\delta t = D(\delta^2 c/\delta x^2)$ where D is the diffusion co-efficient, c is the concentration of substance and x is the coordinate perpendicular to the direction of the fluid flow. If we assume a co-efficient of diffusion for fluorescein of $2.6 \times 10^{-6}$ cm$^2$/s and take into account the flow rate of the fluid through the channel, the concentration profile may be calculated using a Forward Time Centered Space (FTCS) differencing scheme. The theoretical calculations agree well with the experimentally observed profiles. The calculated results are provided in FIG. 17b. The rate of blurring within a profile depends, for example, on the shape of the gradient and in general, the greatest changes occur in areas where the curvature of the gradient is the largest. In the example shown in FIG. 17, this greatest blurring occurs at the junction between the linear and the parabolic parts of the profile. Less sharply shaped areas may retain profile shape for a greater period of time.

In another aspect, the invention may provide a method and apparatus for producing fluid streams of different shear values. For example, a fluid or group of fluids may be input into a microfluidic network such as that shown in FIG. 1, and different channels within the network may possess different resistances to flow. Therefore, the velocity of fluid passing through any one of the outlets will vary with the resistance encountered over that particular path of flow. In this manner, using valves or other constrictions to alter the resistance of channels within the network, fluid streams at different velocities, and therefore at different shear values, may be achieved from a single network with a single pump supplying the fluid.

Figure 18:
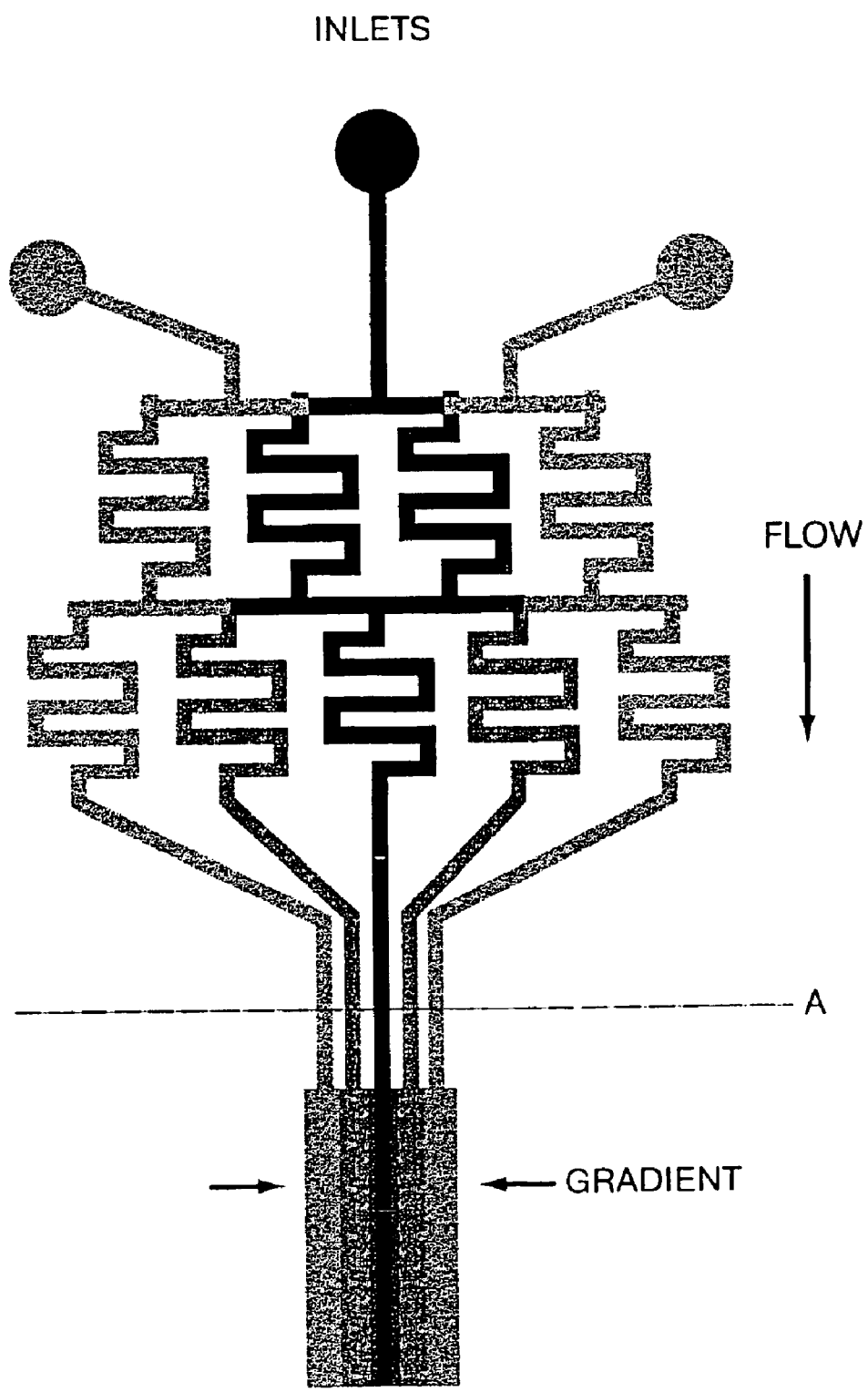
FIG. 18 illustrates schematically a three inlet, five outlet, microfluidic network and illustrates the blurring that occurs between adjacent fluid streams in laminar flow and provides a point (A) where individual streams may be sampled prior to forming a composite stream.

In another aspect, the invention may be used to prepare, distribute or dilute fluid solutions. For example, referring to FIG. 18, three different solutions may be input into the three inlets of the fluidic network and the five outlets may separately feed different receiving vessels. Using such a system, a concentrated solution may be pumped into one or more of the inlets and a dilute solution may be pumped into one or more of the other inlets. By choosing the proper network geometry and flux rates for each of the inlets, different and predictable solutions will be produced at each of the five outlets. Thus, any solution that could be made through the multiple steps of preparing a serial dilution may instead be made by simply combining two solutions containing the substance at different concentrations. In this manner, minimal quantities of the substance may be required, thus saving on expensive chemicals and reagents and reducing waste. In addition, each solution of a different concentration may be produced in equivalent quantities accurately and simultaneously.

Furthermore, by increasing, for example, the number of inlets, additional substances may be introduced into the network, resulting in solutions containing different, but predictable, quantities of two or more substances. Thus, micro-quantities of solutions containing varying, but precise, quantities of two or more substances may be produced on a continuous basis. For example, a solution containing a reagent may be pumped into one inlet, a solution containing a buffer into a second inlet and a solution containing an acid into a third inlet. In this manner, individual fluid streams may be produced containing various concentrations of the reagent at a variety of pHs. The output of each stream may be predicted by the structure of the microfluidic network and by the flux rates employed at each of the inlets.

In another embodiment, the same device may be used to supply titrating fluid with one or more properties of the fluid varying between each of the outlets. For example, a substance may be simultaneously titrated against a variety of solutions each containing a different amount of a titrating agent. Alternatively, one of the components in the solution may be kept constant for each of the output solutions while varying another of the components. Of course, multiple networks may be used in parallel with different outputs from each of the networks being joined together to produce unique solutions. Such a system may be engineered to produce any combination of solutions that could alternatively be made by time, material and labor intensive serial dilution techniques. In addition, the output may be dynamically altered, for example, by employing valves in the network or variable speed pumps at the inlets.

In another aspect, materials may be deposited on a surface to form a stationary gradient. For example, a gradient of a chemical or biochemical may be formed in a fluid by, for example, using a gradient generator such as that shown in FIG. 1, and the solution may be passed over a surface on which the chemical or biochemical may be deposited. This may allow various compounds to be fixed to a surface at concentrations that vary over a very small scale. A surface may be derivatized using this technique with anything that could be suspended or dissolved in a fluid. The fluid may then be fed to a device such as that shown in FIG. 1 and a desired concentration gradient produced. If the surface is placed in contact with the concentration gradient and has an affinity for the material contained in the fluid, the material may be deposited on the surface proportionally to its concentration in the solution at the point of contact. Furthermore, a solution containing two or more components may be manipulated to provide the surface with each component at a different concentration gradient. For instance, one component may be deposited in a linear gradient increasing from left to right while a second component may be applied to the surface parabolically. Furthermore, the two substances may be applied to the surface simultaneously using the same fluid. Examples of materials that may be applied to a surface include biochemicals and chemicals such as peptides and ligands, polymers and pre-polymers, and compounds exhibiting specific reactive groups. For example, a mixed SAM may be deposited in a desired gradient on a surface. Surfaces may include, for example, glass, silicon, metals such as gold, and gels. In addition, any of these components may be applied to a surface in a second order or higher gradient as well as in a linear gradient. In a related aspect, materials that have been attached to a surface may be preferentially removed by passing a fluid containing a gradient of a substance having an affinity for the material that has been attached to the surface.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A method of treating a surface comprising:
   passing a fluid along a portion of a surface under conditions of substantially laminar flow wherein the fluid comprises a concentration gradient of at least one substance, the concentration gradient being substantially perpendicular to the direction of flow and being substantially continuous across the fluid; and
   treating differentially a plurality of sections of the portion of the surface exposed to different concentrations of the substance.

2. The method of claim 1 wherein the portion of the surface is less than 10 cm wide.

3. The method of claim 2 wherein the portion of the surface is less than 1 cm wide.

4. The method of claim 3 wherein the portion of the surface is less than 1 mm wide.

5. The method of claim 4 wherein the substance is a catalyst.

6. The method of claim 4 wherein the treatment comprises hardening the surface.

7. The method of claim 4 wherein the treating comprises depositing the substance on the surface.

8. The method of claim 7 wherein the portion of the surface is less than 1 cm in width.

9. The method of claim 4 wherein the treating comprises forming a topological gradient on the surface.

10. The method of claim 9 wherein the treating comprises removing material from the surface.

11. The method of claim 10 wherein the portion of the surface is less than 1 cm in width.

12. A method of producing a series of solutions comprising:
    contacting a concentrated solution of a substance and a less concentrated solution of the substance under conditions of substantially laminar flow to form a combined fluid; and
    separating the combined fluid, without using a membrane, into a plurality of separate streams wherein at least one of the separate streams comprises the substance at a concentration that is substantially different than the concentration of the substance in another of the separate streams.

13. The method of claim 12 wherein the concentration of the substance in one of the separate streams is about equal to the concentration of the substance in either the concentrated solution or the less concentrated solution.

14. The method of claim 12 further comprising the step of contacting a third solution comprising a second substance with the combined fluid.

15. The method of claim 14 wherein at least one of the separate streams contains concentrations of the first substance and the second substance at a ratio that is different than the ratio of the first substance and the second substance in at least one other of the separate streams.

* * * * *

UNITED STATES PATENT AND TRADEMARK OFFICE
CERTIFICATE OF CORRECTION

| | |
|---|---|
| PATENT NO. | : 6,883,559 B2 |
| APPLICATION NO. | : 10/690475 |
| DATED | : April 26, 2005 |
| INVENTOR(S) | : Jeon et al. |

Page 1 of 1

It is certified that error appears in the above-identified patent and that said Letters Patent is hereby corrected as shown below:

In the Claims:

Column 21, in claims 5, 6, 7 and 9:
Lines 5, 20, 22 and 26 change the noted dependent "claim 4"

to    -- claim 1--

Signed and Sealed this

Thirtieth Day of January, 2007

JON W. DUDAS
*Director of the United States Patent and Trademark Office*